(12) United States Patent
Seo et al.

(10) Patent No.: US 11,461,893 B2
(45) Date of Patent: Oct. 4, 2022

(54) MEDICAL IMAGING APPARATUS AND METHOD OF CONTROLLING THE SAME, AND SERVER AND METHOD OF CONTROLLING THE SAME

(71) Applicant: SAMSUNG ELECTRONICS CO., LTD., Suwon-si (KR)

(72) Inventors: Seong Eun Seo, Suwon-si (KR); Sung Nam Kim, Suwon-si (KR); Ji Yoon Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 153 days.

(21) Appl. No.: 16/738,553

(22) Filed: Jan. 9, 2020

(65) Prior Publication Data

US 2020/0234437 A1    Jul. 23, 2020

(30) Foreign Application Priority Data

Jan. 18, 2019   (KR) .................. 10-2019-0006825

(51) Int. Cl.
  *G06K 9/00* (2022.01)
  *G06T 7/00* (2017.01)
  (Continued)

(52) U.S. Cl.
  CPC ............ *G06T 7/0012* (2013.01); *G06T 9/002* (2013.01); *G06V 10/46* (2022.01); *G16H 30/20* (2018.01);
  (Continued)

(58) Field of Classification Search
  None
  See application file for complete search history.

(56) References Cited

U.S. PATENT DOCUMENTS

2005/0251013 A1   11/2005   Krishnan et al.
2019/0125459 A1*   5/2019   Shelton, IV ....... A61B 17/0206
(Continued)

FOREIGN PATENT DOCUMENTS

JP   2016-97195    5/2016
JP   2018-126329   8/2018

OTHER PUBLICATIONS

European Office Action for European Application No. 20150896.7 dated Mar. 21, 2022.

*Primary Examiner* — Wei Wen Yang
(74) *Attorney, Agent, or Firm* — Staas & Halsey LLP

(57) ABSTRACT

Disclosed herein is a server collectively managing rejection codes for each type of a medical image and determining accuracy of the codes for the medical image transmitted from a medical imaging apparatus, providing a feedback, and a method of controlling the same. A medical imaging apparatus disclosed herein assigns rejection codes based on feedback received from the server and a method disclosed controls the same. The server includes a communication circuitry configured to communicate with a medical imaging apparatus, and a controller configured to control the communication circuitry to receive a medical image and a rejection code assigned to the medical image from the medical imaging apparatus, perform an image processing on the medical image to determine the rejection code of the medical image, and compare the determined rejection code and the received rejection code to generate information associated with a result of the comparison.

19 Claims, 17 Drawing Sheets

(51) Int. Cl.
*G16H 30/20* (2018.01)
*G16H 30/40* (2018.01)
*G06T 9/00* (2006.01)
*G06V 10/46* (2022.01)

(52) U.S. Cl.
CPC ... *G16H 30/40* (2018.01); *G06T 2207/30004* (2013.01)

(56) References Cited

U.S. PATENT DOCUMENTS

2019/0324430 A1* 10/2019 Herzog .................. G07C 5/006
2021/0192733 A1* 6/2021 Gross ..................... A61B 5/055

* cited by examiner

FIG. 6

| Reject Code | Reject Reason |
|---|---|
| RC001 | System Failure |
| RC002 | Positioning |
| RC003 | Metal Object |
| RC004 | Patient Motion |
| RC005 | Clinical Artifacts |
| RC006 | Incorrect Marker |
| RC007 | Others |

MEDICAL IMAGING APPARATUS AND METHOD OF CONTROLLING THE SAME, AND SERVER AND METHOD OF CONTROLLING THE SAME

CROSS-REFERENCE TO RELATED APPLICATION(S)

This application is based on and claims priority under 35 U.S.C. § 119 to Korean Patent Application No. 10-2019-0006825, filed on Jan. 18, 2019 in the Korean Intellectual Property Office, the disclosure of which is incorporated by reference in its entirety.

TECHNICAL FIELD

Embodiments of the disclosure relate to a medical imaging apparatus and a server for managing a medical image, information about the medical image and a rejection code assigned to the medical image, and methods thereof.

BACKGROUND

Generally, a medical imaging apparatus is an apparatus that captures information of a patient to obtain a medical image and displays the obtained medical image. At this time, a user of the medical imaging apparatus may determine whether or not the medical image can be used for diagnosis, and may reject the medical image by assigning a rejection code to the medical image determined to be unusable for diagnosis.

The rejection code assigned to the medical image may not be accurate because there is no procedure for determining whether or not the assigned rejection code corresponds to the reason why the medical image is not useable for diagnosis.

In addition, the rejection codes assigned to the medical images may be different in type depending on the medical imaging apparatus, and thus, there is a limitation in being managed in one server.

SUMMARY

Therefore, it is an aspect of the disclosure to provide a server collectively managing rejection codes for each rejection type of a medical image and determining the accuracy of the rejection codes for the medical image transmitted from a medical imaging apparatus, and providing a feedback, and a method of controlling the server.

In addition, it is another aspect of the disclosure to provide a medical imaging apparatus inducing a user to assign correct rejection codes based on the feedback on the accuracy of the rejection codes received from the server, and a method of controlling the medical imaging apparatus.

Additional aspects of the disclosure will be set forth in part in the description which follows and, in part, will be obvious from the description, or may be learned by practice of the disclosure.

In accordance with an aspect of the disclosure, a server includes: a communication circuitry configured to communicate with a medical imaging apparatus; and a controller configured to control the communication circuitry to receive a medical image and a rejection code assigned to the medical image from the medical imaging apparatus, to perform an image processing on the medical image to determine the rejection code of the medical image, and to compare the determined rejection code and the received rejection code to generate information about the comparison result.

When the determined rejection code and the received rejection code are different, the controller may control the communication circuitry to transmit the information about the comparison result to the medical imaging apparatus.

The controller may extract feature points of the medical image, and determine the rejection code of the medical image based on the extracted feature points and information about a predetermined rejection code for each feature points.

The controller may perform an arithmetic operation on the medical image through a neural network, and determine the rejection code of the medical image based on information related to the arithmetic operation performed through the neural network.

The controller may determine the rejection code of the medical image based on at least one of a result of the image processing, information about a capturing condition assigned to the medical image, and information about a system log of the medical imaging apparatus.

The server may further include: a display. The controller may control the display to display at least one of the medical image, the determined rejection code, and the information about the comparison result.

The server may further include an inputter configured to receive an input from a user. When the user's input granting the determined rejection code is received through the inputter, the controller may transmit the information about the comparison result to the medical imaging apparatus; and when the user's input non-granting the determined rejection code through the inputter is received, the controller may perform the image processing on the medical image again to re-determine the rejection code of the medical image.

When the rejection code reassigned from the medical imaging apparatus to the medical image is received through the communication circuitry after transmitting the comparison result, the controller may control the display to display the comparison result between the rejection code before reassignment and the reassigned rejection code.

The server may further include a storage. When the determined rejection code and the received rejection code are the same, the controller may control the storage to store the medical image and the received rejection code in statistical information corresponding to the medical imaging apparatus, and when the rejection code reassigned to the medical image is received, the controller may control the storage to store the medical image and the reassigned rejection code in statistical information corresponding to the medical imaging apparatus.

The controller may control the communication circuitry to transmit a predetermined rejection code for each rejection type to a plurality of medical imaging apparatuses.

When a new rejection type other than the rejection type included in the predetermined rejection code for each rejection type and a new rejection code corresponding to the new rejection type is received from at least one medical imaging apparatus among the plurality of medical imaging apparatuses, through the communication circuitry, the controller may update the predetermined rejection code for each rejection type to include the new rejection code corresponding to the new rejection type to the predetermined rejection code for each rejection type.

The controller may control the communication circuitry to transmit the updated rejection code for each rejection type to the plurality of medical imaging apparatuses.

In accordance with another aspect of the disclosure, a medical imaging apparatus includes: a display; a communication circuitry configured to communicate with a server; an inputter configured to receive an input from a user; a capturer configured to capture a medical image of an object; and a controller configured to control the communication circuitry to transmit the medical image and the assigned rejection code to the server when a rejection code for the medical image is assigned from the user through the inputter, and to control the display to display the comparison result when receiving a comparison result representing that the assigned rejection code from the server and the rejection code determined by the server are different from each other.

When the rejection code for the medical image is reassigned from the user through the inputter, the controller may control the communication circuitry to transmit the reassigned rejection code to the server.

The medical imaging apparatus may further include a storage. The controller may control the storage to store the rejection code for each rejection type received from the server through the communication circuitry.

When the new rejection type other than the rejection type included in the rejection code for each rejection type and the new rejection code corresponding to the new rejection type are input from the user through the inputter, the controller may control the communication circuitry to transmit the new rejection type and the new rejection code to the server.

When an updated rejection code for each rejection type different from the stored rejection code for each rejection type is received from the server, the controller may control the storage to store the updated rejection code for each rejection type.

In accordance with another aspect of the disclosure, a method of controlling a medical imaging apparatus including a display, a communication circuitry configured to communicate with a server, an inputter configured to receive an input from a user, and a capturer configured to capture a medical image of an object, the method includes when a rejection code for the medical image is assigned from the user through the inputter, controlling, by a controller, the communication circuitry to transmit the medical image and the assigned rejection code to the server; and when receiving a comparison result representing that the assigned rejection code from the server and the rejection code determined by the server are different from each other, controlling, by the controller, the display to display the comparison result.

The method may further include when the rejection code for the medical image is reassigned from the user through the inputter, controlling, by the controller, the communication circuitry to transmit the reassigned rejection code to the server.

The medical imaging apparatus may further include a storage. The method may further include controlling, by the controller, the storage to store the rejection code for each rejection type received from the server through the communication circuitry.

The method may further include when the new rejection type other than the rejection type included in the rejection code for each rejection type and the new rejection code corresponding to the new rejection type are input from the user through the inputter, controlling, by the controller, the communication circuitry to transmit the new rejection type and the new rejection code to the server.

The method may further include when an updated rejection code for each rejection type different from the stored rejection code for each rejection type is received from the server, controlling, by the controller, the storage to store the updated rejection code for each rejection type.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 6 is a view illustrating a predetermined rejection code for each rejection type according to embodiments of the disclosure;

DETAILED DESCRIPTION

Figure 1:
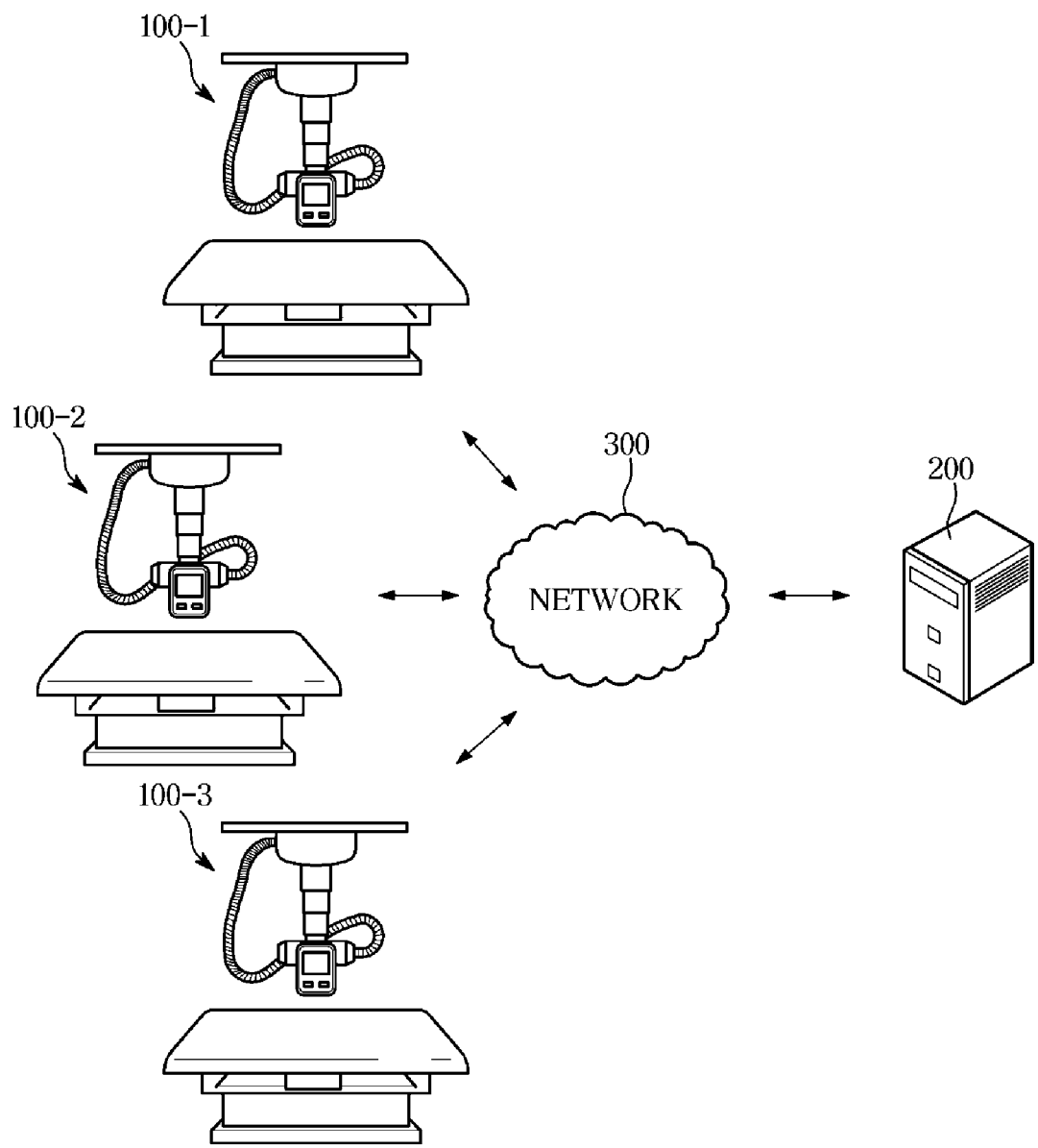
FIG. 1 is a block diagram illustrating a configuration of a medical image management system including a medical imaging apparatus and a server according to embodiments of the disclosure.

Embodiments described herein and configurations illustrated in the accompanying drawings are only certain examples of the disclosure, and various modifications may be made at the time of filing of the present application to replace the embodiments and drawings of the present specification.

It will be understood that when a component is referred to as being "connected" to another component, it can be directly or indirectly connected to the other component. When a component is indirectly connected to another component, it may be connected to the other component through a wireless communication network.

In addition, the terms used herein are intended to only describe certain embodiments, and shall by no means restrict and/or limit the disclosure. It is to be understood that the singular forms "a," "an," and "the" include plural referents unless the context clearly dictates otherwise. In the present specification, the terms such as "comprising," "having" or "including" are intended to designate the presence of characteristics, numbers, steps, operations, elements, parts or combinations thereof, and shall not be construed to preclude any possibility of the presence or addition of one or more other characteristics, numbers, steps, operations, elements, parts or combinations thereof.

In addition, although the terms including ordinal numbers such as "first" or "second" may be used herein to describe various elements, the elements should not be limited by such terms. The terms are used only for the purpose of distinguishing one component from another. For example, without departing from a scope of the disclosure, a first component may be referred to as a second component, and similarly, the second component may also be referred to as the first component.

As used herein, the terms "portion," "unit," "block," "member," or "module" refer to a unit that can perform at least one function or operation. For example, these terms may refer to at least one piece of software stored in a memory or at least one piece of hardware, such as a Field Programmable Gate Array (FPGA) or an Application Specific Integrated Circuit (ASIC), or at least one process that is processed by a processor.

Reference numerals used in operations are provided for convenience of description, without describing the order of the operations, and the operations can be executed in a different order from the stated order unless a specific order is definitely specified in the context.

Hereinafter, embodiments of the disclosure will be described in detail with reference to the accompanying drawings.

FIG. 1 is a block diagram illustrating a configuration of a medical image management system including a medical imaging apparatus and a server according to embodiments of the disclosure.

Referring to FIG. 1, a medical image management system may include a plurality of medical imaging apparatuses 100 including 100-1, 100-2, and 100-3, a server 200, and a network 300.

Each medical imaging apparatus 100 may be an apparatus that captures information of a patient and obtains a medical image (e.g., an X-ray image, an ultrasound image, a magnetic resonance imaging (MRI), and a computed tomography (CT) image) regarding the patient.

For this purpose, the medical imaging apparatus 100 may correspond to an X-ray imaging apparatus and may correspond to an ultrasound imaging apparatus, a magnetic resonance imaging (MRI) apparatus, a computed tomography (CT) apparatus, and the like. However, the type of the medical imaging apparatus 100 is not limited to the above-described example, and any apparatus that captures information of the patient and obtains the medical image regarding the patient may be included without limitation.

The medical imaging apparatus 100 may be connected to the server 200 through the network 300. In other words, the medical imaging apparatus 100 may communicate with the server 200 by being connected to the network 300 through wireless communication or wired communication.

The wireless communication may include cellular communication using, for example, at least one of Long-Term Evolution (LTE), LTE Advance (LTE-A), Code Division Multiple Access (CDMA), Wideband CDMA (WCDMA), Universal Mobile Telecommunications System (UMTS), wireless broadband (WiBro), Global System for Mobile communications (GSM), or the like. The wireless communication may include, for example, at least one of wireless fidelity (WiFi), Bluetooth, Bluetooth low power (BLE), Zigbee, Near Field Communication (NFC), Magnetic Secure Transmission, Radio Frequency (RF), or Body Area Network (BAN). The wireless communication may include GNSS. The GNSS may refer to, for example, a Global Positioning System (GPS), a Global Navigation Satellite System (GLONASS), a BeiDou Navigation Satellite System (hereinafter, referred to as "BeiDou"), and Galileo, an European global satellite-based navigation system.

The wired communication may include, for example, at least one of a Universal Serial Bus (USB), a High Definition Multimedia Interface (HDMI), a Recommended Standard 232 (RS-232), power line communication, or a plain old telephone service.

The network 300 may include at least one of a telecommunications networks, for example, a computer network (e.g., local area network (LAN) or wide area network (WAN)), the Internet, or a telephone network.

Accordingly, the medical imaging apparatus 100 may transmit a rejected medical image and a rejection code assigned to the rejected medical image that cannot be used for diagnosis among the obtained medical images to the server 200 through the network 300. At this time, the rejection code may correspond to a series of digital codes corresponding to rejection reason or rejection type of the rejected medical image.

The medical imaging apparatus 100 may correspond to an apparatus located in one hospital managed by the server 200 and may be an apparatus located in a plurality of hospitals managed by the server 200. In other words, the medical imaging apparatus 100 may be included without limitation as long as the medical imaging apparatus 100 can be connected to the server 200 through the network 300.

FIG. 1 illustrates three medical imaging apparatuses 100-1, 100-2, and 100-3. However, the number of the medical imaging apparatus 100 connected to the server 200 through the network 300 is not limited, which is merely an example.

The server 200 can communicate with the plurality of medical imaging apparatuses 100 through the network 300.

Particularly, the server 200 may receive rejected medical images and rejection codes assigned to the rejected medical images from each of the medical imaging apparatuses 100.

In this way, the server 200 may generate and manage statistical information for each of the medical imaging apparatuses 100. At this time, the statistical information may include information such as a rejection ratio according to each capturing of the medical imaging apparatus 100 and may include information such as the occurrence frequency for rejection type.

In addition, the server 200 displays the rejected medical images of the medical imaging apparatus 100 and the rejection codes assigned to the rejected medical images so that an administrator can identify an operation state of each medical imaging apparatus 100.

In this way, the server 200 may receive predetermined information from each medical imaging apparatus 100, process the received information and provide the processed information to the administrator, or may provide feedback to the medical imaging apparatus 100. The description of this will be described in detail later.

In this case, the server 200 may correspond to a Picture Archiving and Communication System (PACS) server for receiving and storing the medical image obtained from the medical imaging apparatus 100, and may correspond to a device separately provided from the PACS server.

Hereinafter detailed operations of the respective components of the medical imaging apparatus 100 will be described with reference to an external view.

Figure 2:
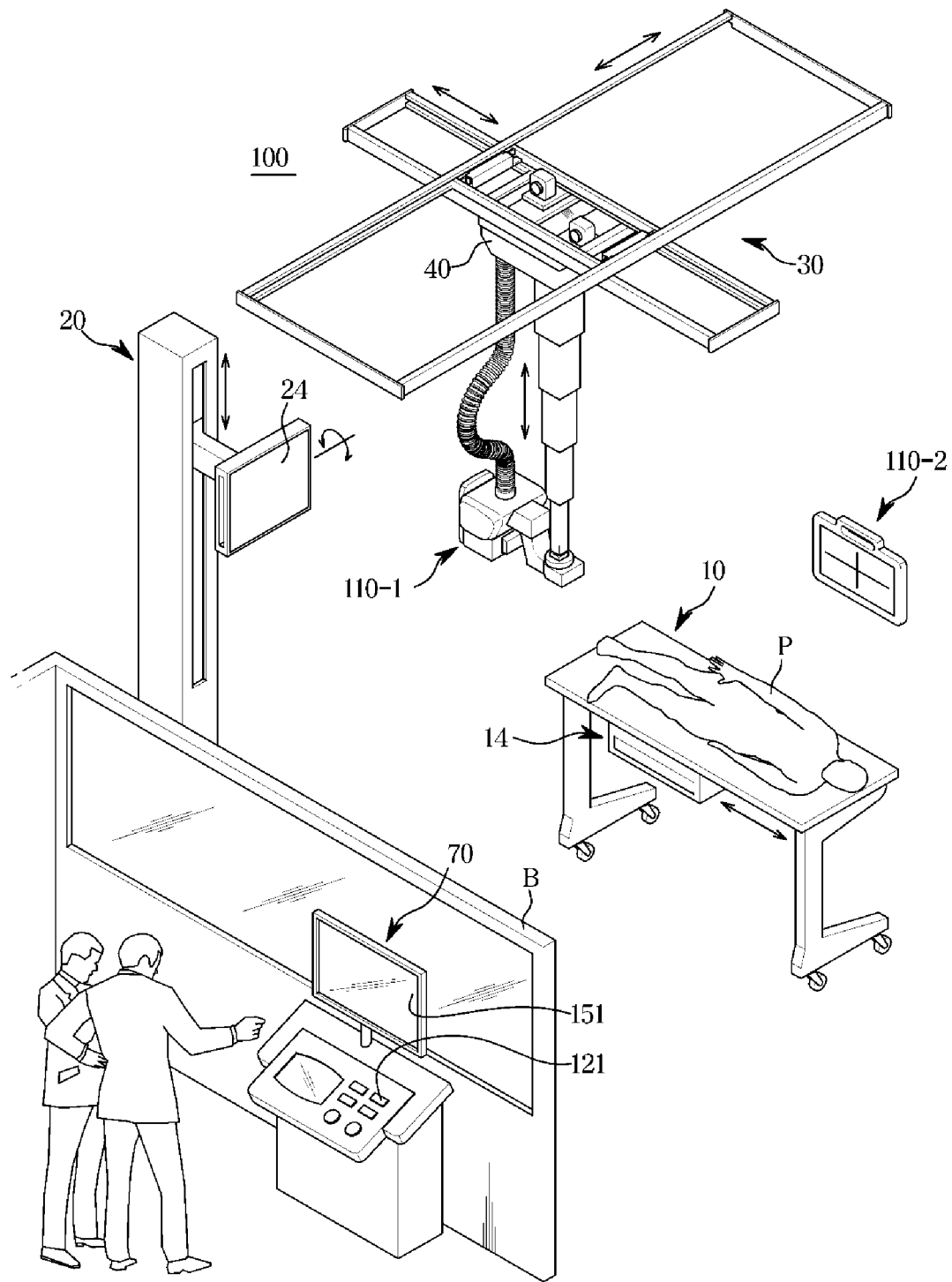
FIG. 2 is an external view illustrating a configuration in which a medical imaging apparatus is implemented as an X-ray imaging apparatus according to embodiments of the disclosure.
Figure 3:
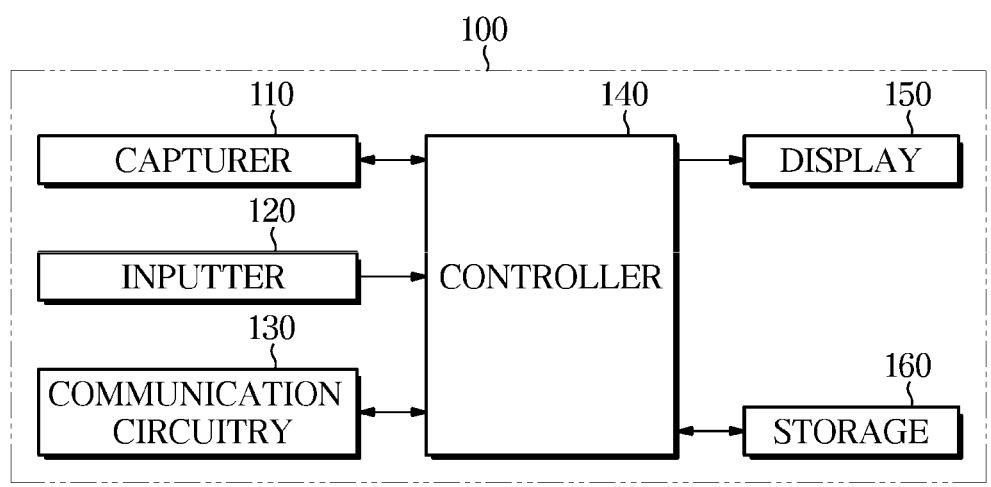
FIG. 3 is a control block diagram of a medical imaging apparatus according to embodiments of the disclosure.

FIG. 2 is an external view illustrating a configuration in which a medical imaging apparatus is implemented as an X-ray imaging apparatus according to embodiments of the disclosure, and FIG. 3 is a control block diagram of a medical imaging apparatus according to embodiments of the disclosure.

Referring to FIGS. 2 and 3, the medical imaging apparatus 100 may include a capturer 110 for capturing information of the patient, an inputter 120 for receiving an input from a user, a communication circuitry 130 for communicating with the server 200 through the network 300, a controller 140 for controlling various configurations of the medical imaging apparatus 100, a display 150 for displaying the obtained medical image and various information, and a storage 160 for storing the various information necessary for controlling the medical imaging apparatus 100.

The capturer 110 may capture information of the patient and obtain the medical image regarding the patient.

As described above, the medical image obtained by the capturer 110 may be any one of various types of medical images such as the X-ray image, the ultrasound image, a magnetic resonance image, and a computed tomography image.

Accordingly, the capturer 110 may correspond to any one of various types of imaging apparatuses such as an X-ray imaging apparatus, an ultrasound imaging apparatus, a MRI imaging apparatus, and the CT apparatus. Hereinafter for convenience of description, the medical imaging apparatus 100 may correspond to the X-ray imaging apparatus, but the disclosure is not limited thereto.

For example, the capturer 110 may include an X-ray source 110-1 for irradiating an X-ray to the patient and an X-ray detector 110-2 for detecting the X-ray passed through the patient, in order to obtain the X-ray image regarding the patient.

Particularly, referring to FIG. 2, guide rails 30 may be installed on a ceiling of an inspection room where the medical imaging apparatus 100 is located, the X-ray source 110-1 may be connected to a moving carriage 40 configured to move along the guide rails 30 to move the X-ray source 110-1 to a position corresponding to the patient.

An exterior illustrated in FIG. 2 is an example of the medical imaging apparatus 100, which corresponds to a case where the medical imaging apparatus 100 corresponds to the X-ray imaging apparatus and relates to a ceiling type X-ray imaging apparatus in which the capturer 100 is connected to the ceiling of the inspection room.

When the medical imaging apparatus 100 is implemented as the ceiling type, the medical imaging apparatus 100 may include at least one motor for providing power necessary to linearly move or rotate the X-ray source 110-1 and a driving circuit for driving the motor. The controller 140 may control the driving circuit to adjust the position and posture of the X-ray source 110-1.

The X-ray source 110-1 may include an X-ray tube for generating the X-ray and a collimator for adjusting a region to be irradiated with the X-ray generated by the X-ray tube. Therefore, the X-ray source 110-1 is also referred to as a tube head unit (THU).

Meanwhile, the medical imaging apparatus 100 may be implemented as the above-described ceiling type X-ray apparatus or a mobile type X-ray apparatus. When the medical imaging apparatus 100 is implemented as the mobile type, a main body connected to the capturer 110 (e.g., an X-ray source) is freely movable and an arm connecting the capturer 110 to the main body is also rotatable and linearly movable, and thus the capturer 110 may be freely movable in a three-dimensional space.

The X-ray detector 110-2 may be implemented as a fixed-type X-ray detector fixed on a stand 20 or a table 10, may be detachably installed at installation parts 14 and 24, or may be implemented as a portable X-ray detector usable at an arbitrary position. The portable X-ray detector may be a wired type X-ray detector or a wireless type X-ray detector according to a data transmission method and a power supply method thereof.

According to an embodiment, the medical imaging apparatus 100 may include a work station 70 provided at a position spaced apart from the X-ray source 110-1 and providing a user interface. A shielding curtain B may be provided between the X-ray source 110-1 and the work station 70 to prevent unnecessary radiation exposure for the user such as a radiologist or a doctor.

The work station 70 may be provided with a first inputter 141 for receiving the users input and a first display 151 for displaying various information and images. The inputter 120 of the medical imaging apparatus 100 may include the first inputter 141 provided in the work station 70, and the display 150 of the medical imaging apparatus 100 may include the first display 151 provided in the work station 70.

The inputter 120 may receive the input from the user. Particularly, the inputter 120 may receive the rejection code for the medical image obtained from the user.

That is, the user of the medical imaging apparatus 100 may examine the medical image displayed on the display 150 to determine whether the medical image has a quality enough to be used for medical examination. Further, when the medical image has the rejection reason or rejection type that cannot be used for medical examination, the user may input the rejection code corresponding to the rejection reason or rejection type through the inputter 120.

For this, the inputter 120 may be provided in the main body of the medical imaging apparatus 100 and may be implemented with mechanical buttons, knobs, touch pad, touch screen, stick-type manipulation device, trackball, or the like. At this time, the inputter 120 provided with a touch pad or a touch screen may be provided on the display 150.

The inputter 120 may be connected to the medical imaging apparatus 100 by wire or wirelessly, and may be provided as a separate input device such as a keyboard and a mouse.

The communication circuitry 130 may communicate with the server 200 through the network 300.

At this time, the communication circuitry 130 may perform communication with the server 200 by wire or wirelessly.

To this end, the communication circuitry 130 may include, for example, a cellular module, a WiFi module, a Bluetooth module, a GNSS module, an NFC module, and an RF module.

At least some (e.g., two or more) of the cellular module, the WiFi module, the Bluetooth module, the GNSS module, or the NFC module may be included in one Integrated Chip (IC) or IC package. The RF module may transmit and receive, for example, a communication signal (e.g., an RF signal). The RF module may include, for example, a transceiver, a Power Amp Module (PAM), a frequency filter, a Low Noise Amplifier (LNA), or an antenna. At least one of the cellular module, the WiFi module, the Bluetooth module, the GNSS module, or the NFC module may transmit and receive the RF signal through separate RF module.

Also, the communication circuitry 130 may include a USB module, an HDMI module, an R2-232 module, and a POTS module for wired communication.

The communication circuitry 130 may transmit the medical image and the rejection code assigned to the medical image to the server 200 under the control of the controller 140 and may receive the rejection code for the medical image determined by the server 200.

The communication circuitry 130 may also receive a predetermined rejection code for each rejection type from the server 200 under the control of the controller 140. When the rejection code for each rejection type is updated, the communication circuitry 130 may receive the rejection code for the updated rejection type.

When a new rejection type and a new rejection code that are not included in the predetermined rejection code for each rejection type are input through the inputter 120, the communication circuitry 130 may also transmit the new rejection type and the new rejection code to the server 200.

The controller 140 may control various configurations of the medical imaging apparatus 100.

Particularly, the controller 140 may control the communication circuitry 130 to transmit the medical image and the assigned rejection code to the server 200 when the rejection code for the medical image is assigned from the user through the inputter 120.

That is, when the rejection code for the medical image is received from the user through the inputter 120 according to the determination that the medical image cannot be used for diagnosis, the controller 140 may control the communication circuitry 130 to transmit the medical image and the rejection code for the medical image to the server 200.

When receiving a comparison result, which represents that the rejection code assigned by the user and the rejection code determined by the server 200 are different from each other, from the server 200 through the communication circuitry 130, the controller 140 may control the display 150 to display the comparison result.

For this, the user may identify that the rejection code inputted by the user is different from the rejection code determined by the server 200, and may re-input a correct rejection code through the inputter 120.

The controller 140 may control the communication circuitry 130 to transmit the reassigned rejection code to the server 200 when the rejection code for the medical image is reassigned from the user through the inputter 120.

In this way, the user of the server 200 may determine whether or not the rejection code for the medical image has been correctly assigned in response to the feedback of the server 200 by the user of the medical imaging apparatus 100.

The controller 140 may also control the storage 160 to store the rejection code for each rejection type received from the server 200 through the communication circuitry 130.

That is, the medical imaging apparatus 100 uses the rejection code for each rejection type received from the server 200 through the communication circuitry 130, thus the plurality of medical imaging apparatuses 100 connected to the server 200 may use the same rejection code for the rejection type.

Accordingly, the server 200 may more efficiently manage the medical images of the medical imaging apparatus 100 and the corresponding rejection codes, and may ensure consistency of the statistical information.

In addition, when the new rejection type, which is other than the rejection type included in the stored rejection code for each rejection type and the new rejection code corresponding to the new rejection type are inputted from the user through the inputter 120, the controller 140 may control the communication circuitry 130 to transmit the new rejection type and the new rejection code to the server 200.

That is, when there is no the rejection type corresponding to the obtained medical image on the rejection code for each rejection type provided from the server 200, the user may manually input the rejection type and the rejection code corresponding to the rejection type, thereby generating the new rejection type and the new rejection code.

The communication circuitry 130 of the imaging apparatus 100 may transmit the generated new rejection type and new rejection code to the server 200 so that the new rejection type and the new rejection code generated by the medical imaging apparatus 100 are also shared with other medical imaging apparatuses 100 so that the plurality of medical imaging apparatuses 100 connected to the server 200 use a consistent rejection code for each type rejection type.

At this time, the server 200 may update the predetermined rejection code for each rejection type to include the received new rejection type and the new rejection code, and may transmit the updated rejection code for each rejection type to the plurality of medical imaging apparatuses 100 connected through the network 300.

When receiving the updated rejection code for each rejection type different from the stored rejection code for each rejection type from the server 200, the controller 140 of each medical imaging apparatus 100 connected to the server 200 through the network 300 may control the storage 160 to store the updated rejection code for each rejection type.

The controller 140 may include at least one memory storing a program for performing the above-described operations and operations, which will be described below, and at least one processor for executing the stored program.

The display 150 may display the obtained medical image and a variety of information.

Particularly, the display 150 may display the stored rejection code for each rejection type for inputting the obtained medical image and the rejection code for the obtained medical image.

Accordingly, through the inputter 120, the user may input or assign the rejection code for the medical image by selecting the rejection code corresponding to the rejection type of the medical image among the rejection codes for each rejection type displayed on the display 150.

The display 150 may also display the comparison result between the rejection code for the medical image assigned by the user and the rejection code determined by the server 200.

The display 150 may be provided in the main body of the medical imaging apparatus 100 and may be provided as a separate display module connected to the main body of the medical imaging apparatus 100 in a wired or wireless manner.

The display 150 may include, for example, a liquid crystal display (LCD), a light emitting diode (LED) display, an organic light emitting diode (OLED) display, a micro electromechanical systems (MEMS) display, or an electronic paper display. However, the type of the display 150 is not limited to the above-described example, and any type of display 150 capable of displaying the medical image to the user may be included without limitation.

The storage 160 may store a variety of information necessary for controlling the medical imaging apparatus 100. For example, the storage 160 may store the rejection code for each rejection type received from the server 200.

To this end, the storage 160 may be implemented as at least one of a non-volatile memory device (for example, a cache, Read Only Memory (ROM), Programmable ROM (PROM), Erasable Programmable ROM (EPROM), Electrically Erasable Programmable ROM (EEPROM), and flash memory), a volatile memory device (for example, Random Access Memory (RAM)), or a storage medium (for example, Hard Disk Drive (HDD) and Compact Disc Read Only Memory (CD-ROM)). However, it is not limited to this, and if it is the type capable of storing a variety of information, it can be used as the type of the storage 160.

Further, the storage 160 may be the memory implemented in a separate chip from the above-described processor in connection with the controller 140, and may be implemented as a single chip with the processor.

Figure 4:
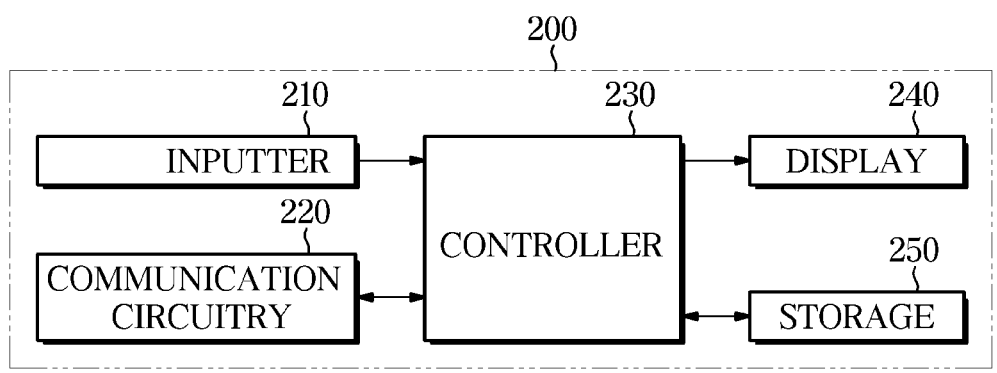
FIG. 4 is a control block diagram of a server according to embodiments of the disclosure.

FIG. 4 is a control block diagram of a server according to embodiments of the disclosure.

Referring to FIG. 4, the server 200 may include an inputter 210 for receiving the input from the user, a communication circuitry 220 for communicating with the plurality of medical imaging apparatuses 100 through the network 300, a controller 230 for determining the rejection code of the medical image received from the medical imaging apparatus 100 and comparing the determined rejection code with the rejection code received from the medical imaging apparatus 100 to generate information about the comparison result, a display 240 for displaying the medical image and the information about the comparison result received form the medical imaging apparatus 100, and a storage 250 for storing the various information necessary for controlling the server 200.

The inputter 210 may receive the input from the user of the server 200.

Particularly, the inputter 210 may receive the rejection code for the medical image received from the medical imaging apparatus 100 and displayed on the display 240.

That is, the user of the server 200 may input, through the inputter 210, the rejection code corresponding to the rejection reason or the rejection type of the medical image displayed on the display 240.

Also, the inputter 210 may receive from the user whether or not the rejection code determined based on an image processing for the medical image is approved.

That is, the user of the server 200 may determine whether the rejection code of the medical image determined through the image processing by the server 200 is correct and input the approval or rejection through the inputter 210 to increase the accuracy of the rejection code determined by the server 200.

For this, the inputter 210 may be provided in the main body of the server 200 and may be implemented with mechanical buttons, knobs, touch pad, touch screen, stick-type manipulation device, trackball, or the like. At this time, the inputter 210 provided with the touch pad or the touch screen may be provided on the display 240.

The inputter 210 may be connected to the server 200 by wire or wirelessly, and may be provided as the separate input device such as the keyboard and the mouse.

The communication circuitry 220 may communicate with the plurality of medical imaging apparatuses 100 through the network 300.

At this time, the communication circuitry 220 may perform communication with the plurality of medical imaging apparatuses 100 by wire or wirelessly.

To this end, the communication circuitry 220 may include, for example, the cellular module, the WiFi module, the Bluetooth module, the GNSS module, the NFC module, and the RF module.

At least some (e.g., two or more) of the cellular module, the WiFi module, the Bluetooth module, the GNSS module, or the NFC module may be included in one Integrated Chip (IC) or IC package. The RF module may transmit and receive, for example, the communication signal (e.g., the RF signal). The RF module may include, for example, the transceiver, the Power Amp Module (PAM), the frequency filter, the Low Noise Amplifier (LNA), or the antenna. At least one of the cellular module, the WiFi module, the Bluetooth module, the GNSS module, or the NFC module may transmit and receive the RF signal through separate RF module.

Also, the communication circuitry 220 may include the USB module, the HDMI module, the R2-232 module, and the POTS module for wired communication.

Accordingly, the communication circuitry 220 may receive the rejected medical image from each of the plurality of medical imaging apparatuses 100 and the rejection code for the rejected medical image according to the control of the controller 230.

Also, the communication circuitry 220 may transmit the rejection code of the medical image determined by the controller 230 to the corresponding medical imaging apparatus 100.

The communication circuitry 220 may also transmit the predetermined rejection code for each rejection type to each medical imaging apparatus 100 under the control of the controller 230 and may receive information about the new rejection type and the new rejection code from the medical imaging apparatus 100. The communication circuitry 220 may also transmit information about the rejection code for each rejection type updated by the controller 230 based on the new rejection type and the new rejection code to each medical imaging apparatus 100.

The controller 230 may determine the rejection code of the medical image received from the medical imaging apparatus 100 and compare the determined rejection code with the rejection code received from the medical imaging apparatus 100 to generate information about the comparison result.

At this time, the controller 230 may individually generate information about the comparison results for each of the plurality of medical imaging apparatuses 100, and control the communication circuitry 220 to transmit the generated information about the comparison results to the corresponding medical imaging apparatus 100.

Particularly, the controller 230 may control the communication circuitry 220 to receive the medical image and the rejection code assigned to the medical image from the medical imaging apparatus 100.

At this time, the received medical image may correspond to the image determined to be unusable for diagnosis, that is, a rejected image, and the rejection code may correspond to the rejection reason, that is, the rejection type.

In addition, the controller 230 may perform the image processing on the received medical image to determine the rejection code of the medical image.

Particularly, the controller 230 may extract feature points of the medical image and determine the rejection code of the medical image based on the extracted feature points and information about a predetermined rejection code for each feature point.

At this time, the controller 230 may extract the feature points in the medical image by applying an image processing algorithm such as an object recognition algorithm. For example, the controller 230 may apply an edge detection to extract artifacts included in the medical image. In addition, the controller 230 may extract the artifacts included in the medical image by extracting the types through morphological operations.

However, the image processing algorithm used to extract the feature points is not limited to the above-described example, and may be used without limitation as long as it corresponds to the image processing algorithm capable of extracting the feature points that can be included in the medical image.

At this time, the feature point may correspond to at least one of metal artifact caused by a metal located in the medical image, motion artifact due to movement of the patient, such as respiration, and noise. However, the types of feature point are not limited to the above-described example, and may be included without limitation as long as they are types of quality defects that can appear in the medical image.

Also, the controller 230 may determine the rejection code of the medical image through a neural network, without determining the rejection code based on the information about the predetermined rejection code for each feature point.

Particularly, the controller 230 may perform an operation on the received medical image through the neural network, and may determine the rejection code of the medical image based on the information about the operation performed through the neural network.

At this time, the information according to the operation through the neural network may include the information about rejection reason or rejection type of the medical image.

Since the above-described neural network may refer to a machine learning that forms a neural structure capable of performing deep learning, a weight and a bias corresponding to the configuration of the neural network continuously change, thereby improving the reliability of learning.

Particularly, the server 200 may continuously receive the medical image and the corresponding rejection code from the outside. The controller 230 may improve inference results of the neural network by continuously updating the weight, the bias, and activation functions included in the neural network based on the medical image and the corresponding rejection code received from the outside.

At this time, the neural network may be stored in storage 250 in the form of a computer program. Hereinafter the computation performed by the neural network in a coding form of the computer program will be described. However, the disclosure is not limited to the computer program in which the neural network is stored.

Meanwhile, the neural network may include a Convolution Neural Network (CNN) for generating a feature map output by convoluting the medical image, and inputting the feature map to the neural network. However, the disclosure is not limited thereto, and may be performed by another deep learning algorithm including Recurrent Neural Networks (RNN).

In addition, the controller 230 may determine the rejection code of the medical image based on at least one of the result of the image processing (for example, the extracted result of the feature point according to the image processing algorithm, and the determination result of the rejection type according to the neural network), the information about a capturing condition assigned to the medical image, and the information about a system log of the medical imaging apparatus 100.

Particularly, in addition to the result of the image processing, the controller 230 may separately or further consider the information about the system log of the medical imaging apparatus 100 received together with the medical image from the medical imaging apparatus 100 to determine that the rejection type of the medical image is a system failure, and may determine the rejection code corresponding to the system failure as the rejection code of the medical image.

In addition to the result of the image processing and the information about the system log, the controller 230 may separately or further consider the information about the capturing condition included in a header of the medical image to determine that the rejection type of the medical image is a capturing condition error, and may determine the rejection code corresponding to the capturing condition error as the rejection code of the medical image.

The controller 230 may compare the determined rejection code and the rejection code received from the medical imaging apparatus 100 to generate information about the comparison result.

At this time, the received rejection code and the determined rejection code may differ depending on a determination error of the user of the medical imaging apparatus 100.

The controller 230 may control the communication circuitry 220 to transmit the information about the comparison result to the medical imaging apparatus 100 when the determined rejection code and the received rejection code are different.

That is, when the rejection code determined by the controller 230 is different from the rejection code received from the medical imaging apparatus 100, the controller 230 may provide feedback that the rejection code determined by the medical imaging apparatus 100 is different from the rejection code inputted so that the user of the medical imaging apparatus 100 can determine his/her judgment once more.

The controller 230 may also receive the rejection code reassigned from the medical imaging apparatus 100 to the medical image through the communication circuitry 220 after transmission of the comparison result to the medical imaging apparatus 100, compare the rejection code before reassignment and the reassigned rejection code to generate the comparison result, and control the display 240 to display the comparison result. At this time, the rejection code before reassignment may correspond to the rejection code received prior to the feedback to the medical imaging apparatus 100.

In addition, the server 200 may further include a user's approval processing for the rejection code determined by the controller 230.

Particularly, through the inputter 210, the controller 230 may receive the user's input granting the determined rejection code.

That is, the user of the server 200 may review the medical image displayed on the display 240 and the determined rejection code to determine whether the determined rejection code corresponds to the rejection reason or rejection type of the medical image. When it is determined that the determined rejection code corresponds to the rejection type of the medical image, the user may input the input for granting the determined rejection code through the inputter 210.

In this case, the controller 230 may proceed to the feedback to the medical imaging apparatus 100 by controlling the communication circuitry 220 to transmit the information about the comparison result of the determined rejection code and the received rejection code to the medical imaging apparatus 100.

Through the inputter 210, the controller 230 may also receive the input from the user who is non-granting the determined rejection code.

That is, when the user of the server 200 determines that the determined rejection code does not correspond to the rejection type of the medical image, the user may input the input for non-granting the determined rejection code through the inputter 210.

In this case, the controller 230 may perform the image processing on the medical image again to determine the rejection code of the medical image again.

In addition, the controller 230 may update the statistical information about each medical imaging apparatus 100 based on the medical image and the corresponding rejection code.

Particularly, when the determined rejection code and the received rejection code are the same, the controller 230 may control the storage 250 to store the medical image and the received rejection code in the statistical information corresponding to the medical imaging apparatus 100.

When receiving the reassigned rejection code for the medical image, the controller 230 may also control the storage 250 to store the medical image and the reassigned rejection code in the statistical information corresponding to the medical imaging apparatus 100.

In this case, the statistical information may include information about the ratio of rejected medical images among the medical images captured by the medical imaging apparatus 100 and statistical information about the rejection reasons or rejection type of the rejected medical images.

In addition, the controller 230 may allow the rejection code received from the medical imaging apparatus 100 to correspond to the predetermined rejection code by presetting the rejection code for each rejection type that may appear in the medical image and distributing the rejection code to the connected medical imaging apparatus 100, and thus the controller 230 may manage the statistical information with a uniform rejection code.

To this end, the controller 230 may control the communication circuitry 220 to transmit the predetermined rejection code for each rejection type to the plurality of medical imaging apparatuses 100 connected through the network 300.

Thereby, each of the plurality of medical imaging apparatuses 100 may store the predetermined rejection code for each rejection type and display the stored rejection code for each rejection type together with the medical image so that the user can input the rejection code by selecting the rejection code corresponding to the rejection type.

The controller 230 may also receive the new rejection type and corresponding new rejection code, which are not included in the predetermined rejection code for each rejection type rejection code, from any one of the medical imaging apparatuses 100 connected through the network 300, and may continuously update information about the rejection code by each rejection type.

In this way, the controller 230 may update the rejection code for each rejection type by adding the rejection code for the rejection type, which was not included in the notification, to the information about the rejection code for each rejection type.

At this time, the controller 230 may control the communication circuitry 220 to transmit the updated rejection code for each rejection type to the plurality of medical imaging apparatuses 100 connected through the network 300. Thereby, the plurality of medical imaging apparatuses 100 may uniformly use the rejection code by storing and using the updated rejection code for each rejection type.

The controller 230 may include at least one memory storing a program for performing the above-described operations and operations, which will be described below, and at least one processor for executing the stored program.

The display 240 may display the received medical image and a variety of information.

Particularly, the display 240 may display the medical image received from the medical imaging apparatus 100, the information about the comparison result between the received rejection code and the determined rejection code, and the information about the comparison result between the reassigned rejection code and the rejection code before reassignment, individually or simultaneously.

The display 240 may be provided in the main body of the server 200 and may be provided as a separate display module connected to the server 200 in a wired or wireless manner.

The display 240 may include, for example, a liquid crystal display (LCD), a light emitting diode (LED) display, an organic light emitting diode (OLED) display, a micro electromechanical systems (MEMS) display, or an electronic paper display. However, the type of the display 240 is not limited to the above-described example, and any type of display 240 capable of displaying the medical image to the user may be included without limitation.

The storage 250 may store a variety of information necessary for controlling the server 200. For example, the storage 250 may store the rejection code for each rejection type, and may store the information about various image processing algorithms for determining the rejection code, the information about the predetermined rejection code for each feature point, and a computer program for the neural network.

To this end, the storage 250 may be implemented as at least one of a non-volatile memory device (for example, a cache, Read Only Memory (ROM), Programmable ROM (PROM), Erasable Programmable ROM (EPROM), Electrically Erasable Programmable ROM (EEPROM), and flash memory), a volatile memory device (for example, Random Access Memory (RAM)), or a storage medium (for example, Hard Disk Drive (HDD) and Compact Disc Read Only Memory (CD-ROM)). However, it is not limited to this, and if it is the type capable of storing a variety of information, it can be used as the type of the storage 250.

Further, the storage 250 may be the memory implemented in a separate chip from the above-described processor in connection with the controller 230, and may be implemented as a single chip with the processor.

Hereinafter the server 200 may distribute the predetermined rejection code for each rejection type to the plurality of medical imaging apparatuses 100 connected through the network 300. When the new rejection code is received from any one of the medical imaging apparatuses 100, the server 200 may update the rejection code for each rejection type and distribute the updated rejection code to the plurality of medical imaging apparatuses 100 so that the uniform rejection code can be used among the plurality of medical imaging apparatuses 100 connected through the network 300.

Figure 5:
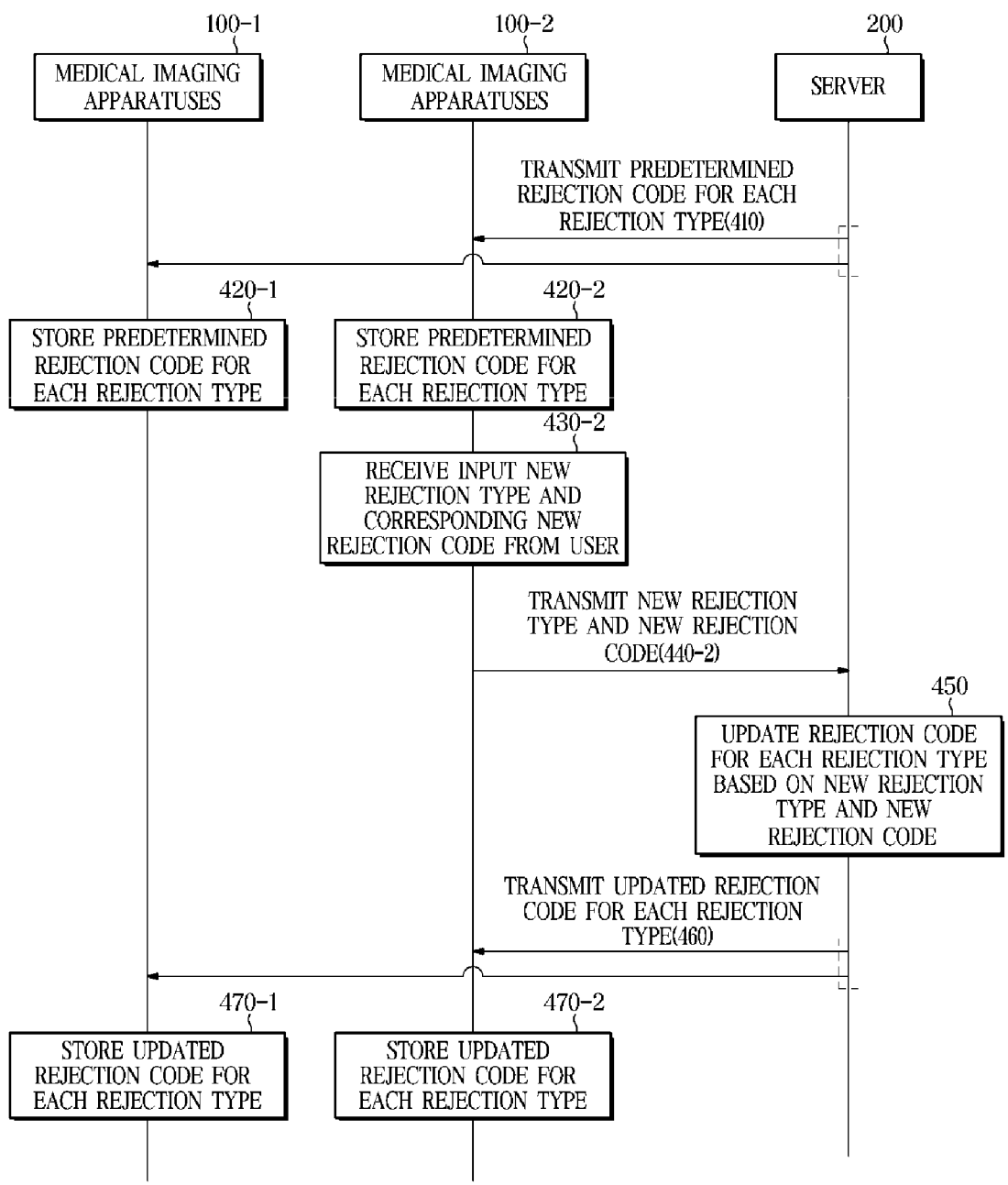
FIG. 5 is a view illustrating a signal flow for managing a rejection code according to embodiments of the disclosure.
Figure 7:
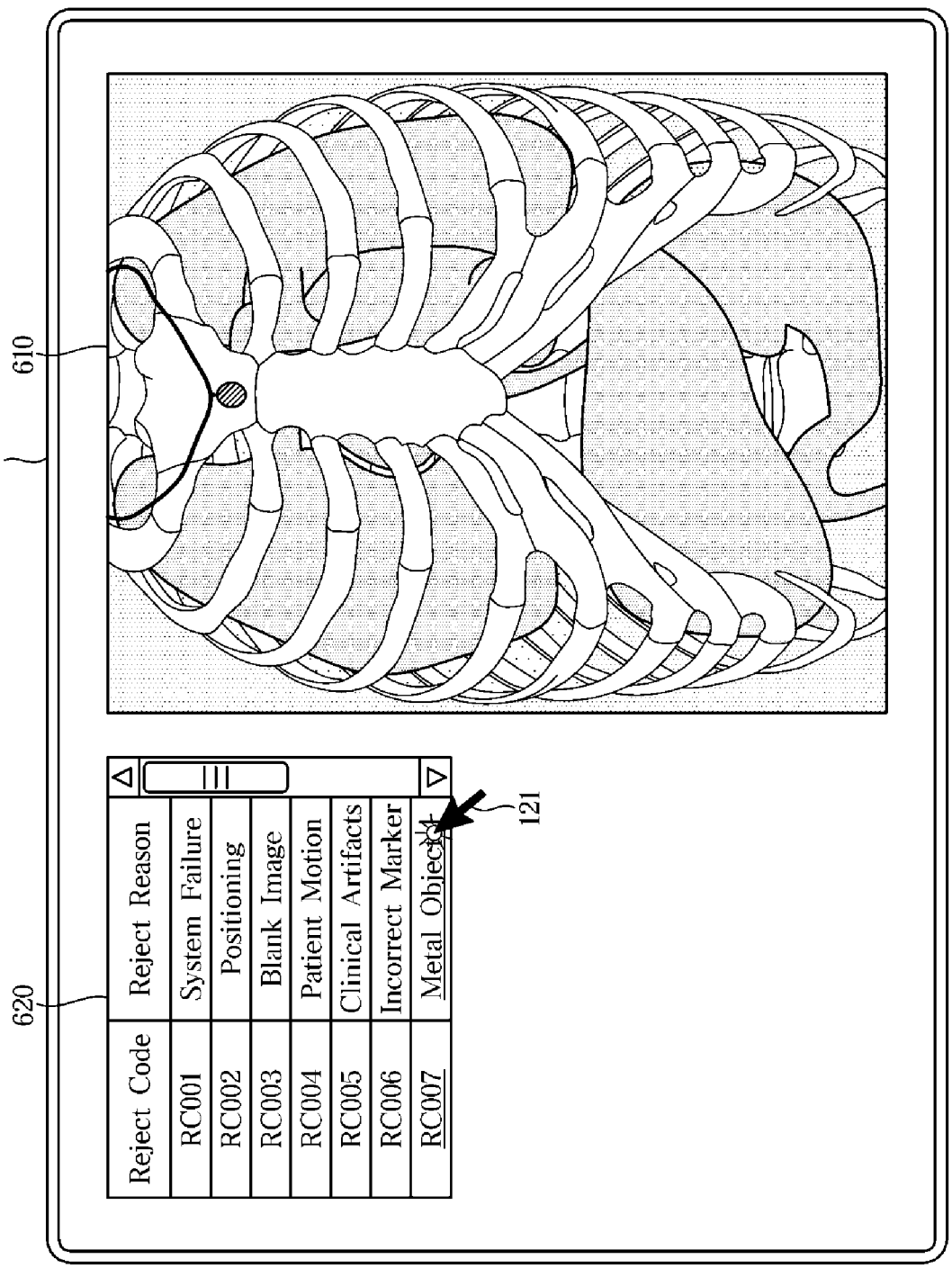
FIG. 7 is a view illustrating a case where a new rejection type and a new rejection code are received in a medical imaging apparatus according to embodiments of the disclosure.

FIG. 5 is a view illustrating a signal flow for managing a rejection code according to embodiments of the disclosure, FIG. 6 is a view illustrating a predetermined rejection code for each rejection type according to embodiments of the disclosure, and FIG. 7 is a view illustrating a case where a new rejection type and a new rejection code are received in a medical imaging apparatus according to embodiments of the disclosure.

Referring to FIG. 5, the server 200 may transmit the predetermined rejection code for each rejection type through the communication circuitry 220 to the plurality of medical imaging apparatuses 100-1 and 100-2 connected through the network 300 (410).

FIG. 5 illustrates two medical imaging apparatuses 100-1 and 100-2. However, this is for convenience of description, and there is no limit to the number of medical imaging apparatuses 100 connected through the network 300.

In addition, the predetermined rejection code for each rejection type may be assigned according to various rejection reasons or corresponding reject code for each reject type, which may appear in the medical image, as illustrated in FIG. 6. At this time, the rejection type may correspond to the type of artifact or noise that may appear in the medical image, and may be a reason for not being used for diagnosis. Also, the rejection code may correspond to a kind of digital code corresponding to the rejection type, and the server 200 may recognize what the rejection type of the medical image is based on the rejection code.

Particularly, referring to FIG. 6, the predetermined rejection code may include 'RC001' as the rejection code corresponding to the system failure, 'RC003' as the rejection code corresponding to the metal object, and 'RC004' as the rejection code corresponding to the motion artifact (Patient Motion).

However, the predetermined rejection code illustrated in FIG. 6 is merely an example, and the rejection type included in the predetermined rejection code and the corresponding rejection code may be included without limitation as long as they are types of quality defects that can appear in the medical image.

On the other hand, the predetermined rejection code for each rejection type may be preset in a design stage of the server 200 and stored in the storage 250, and may be also received from an external server through the communication circuitry 220 and stored in the storage 250.

When the predetermined rejection code for each rejection type is received from the server 200, each of the plurality of medical imaging apparatuses 100-1 and 100-2 may store the predetermined rejection code for each rejection type to each of the storage 160 (420-1, and 420-2).

That is, because each of the medical imaging apparatuses 100 use the rejection code for each rejection type received from the server 200 through the communication circuitry 130, the plurality of medical imaging apparatuses 100-1 and 100-2 connected to the server 200 may use the same rejection code for each rejection type.

Accordingly, the server 200 may more efficiently manage the medical image of each of the medical imaging apparatuses 100 and the corresponding rejection code and ensure the consistency of the statistical information.

Any one the medical imaging apparatus 100-2 of the plurality of medical imaging apparatuses 100-1 and 100-2 may receive the new rejection type and the corresponding new rejection code from the user through the inputter 120 (430-2).

For example, as illustrated in FIG. 7, the user of the medical imaging apparatus 100-2 may review a medical image 610 displayed on the display 150 of the medical imaging apparatus 100-2 and determine that the medical image 610 includes the rejection type of the metal artifact by the patient wearing a metal necklace.

At this time, when the user of the medical imaging apparatus 100-2 identifies that the rejection code related to the metal artifact does not exist in the predetermined rejection code for each rejection type 620 displayed on the display 150 of the medical imaging apparatus 100-2, the user may input the metal artifact as the new rejection type through the inputter 120, and input 'RC007' as the corresponding new rejection code.

The medical imaging apparatus 100-2 may transmit the new rejection type and the new rejection code input through the inputter 120 to the server 200 (440-2).

When the user inputs the new rejection type and the corresponding new rejection code through the inputter 120 and selects the new rejection code through the inputter 120 as the rejection code of the medical image 610 (e.g., through selection at a point 121), the medical imaging apparatus 100-2 may transmit the new rejection type and the new rejection code together with the medical image 610 to the server 200.

In other words, when there is no the rejection type corresponding to the obtained medical image on the rejection code for each rejection type provided from the server 200, the user of the medical imaging apparatus 100-2 may manually input the rejection type and the rejection code corresponding to the rejection type, thereby generating the new rejection type and the new rejection code.

The communication circuitry 130 of the imaging apparatus 100-2 may transmit the generated new rejection type and new rejection code to the server 200 so that the new rejection type and the new rejection code generated by the medical imaging apparatus 100-2 are also shared with the other medical imaging apparatus 100-1 so that the plurality of medical imaging apparatuses 100-1 and 100-2 connected to the server 200 use the consistent rejection code for each type rejection type.

At this time, the server 200 may update the predetermined rejection code for each rejection type based on the received new rejection type and the new rejection code (450).

That is, the server 200 may update the predetermined rejection code for each rejection type to include the received new rejection type and the new rejection code, and may transmit the updated rejection code for each rejection type to the plurality of medical imaging apparatuses 100-1 and 100-2 connected through the network 300 (460).

However, the server 200 may determine whether to add the new rejection code to the predetermined rejection code for each rejection type.

Particularly, the controller 230 may perform the image processing on the medical image 610 transmitted together with the new rejection code to determine the rejection type of the medical image 610, and may determine whether to add the new rejection code to the predetermined rejection code for each rejection type by determining whether the determined rejection type corresponds to the received new rejection type. At this time, the controller 230 may further consider the frequency of the new rejection type, that is, the frequency of reception from the medical imaging apparatus 100 for the new rejection type, to determine whether to add the new rejection code to the rejection code for each rejection type.

That is, the server 200 may update the predetermined rejection code for each rejection type by adding the new rejection code to the predetermined rejection code for each rejection type when the determined rejection type corresponds to the received new rejection type.

When the updated rejection code for each rejection type is received from the server 200, each of the plurality of medical imaging apparatuses 100-1 and 100-2 may store the updated rejection code for each rejection type to each of the storage 160 (470-1, and 470-2).

Thereby, the plurality of medical imaging apparatuses 100-1 and 100-2 may uniformly use the rejection code by storing and using the updated rejection code for each rejection type.

Hereinafter the server 200 may receive the medical image and the rejection code from the medical imaging apparatus 100. When the rejection code determined based on the received medical image is different from the received rejection code, the server 200 may provide feedback to the medical imaging apparatus 100 so that the user of the medical imaging apparatus 100 can select the correct rejection code will be described.

Figure 8:
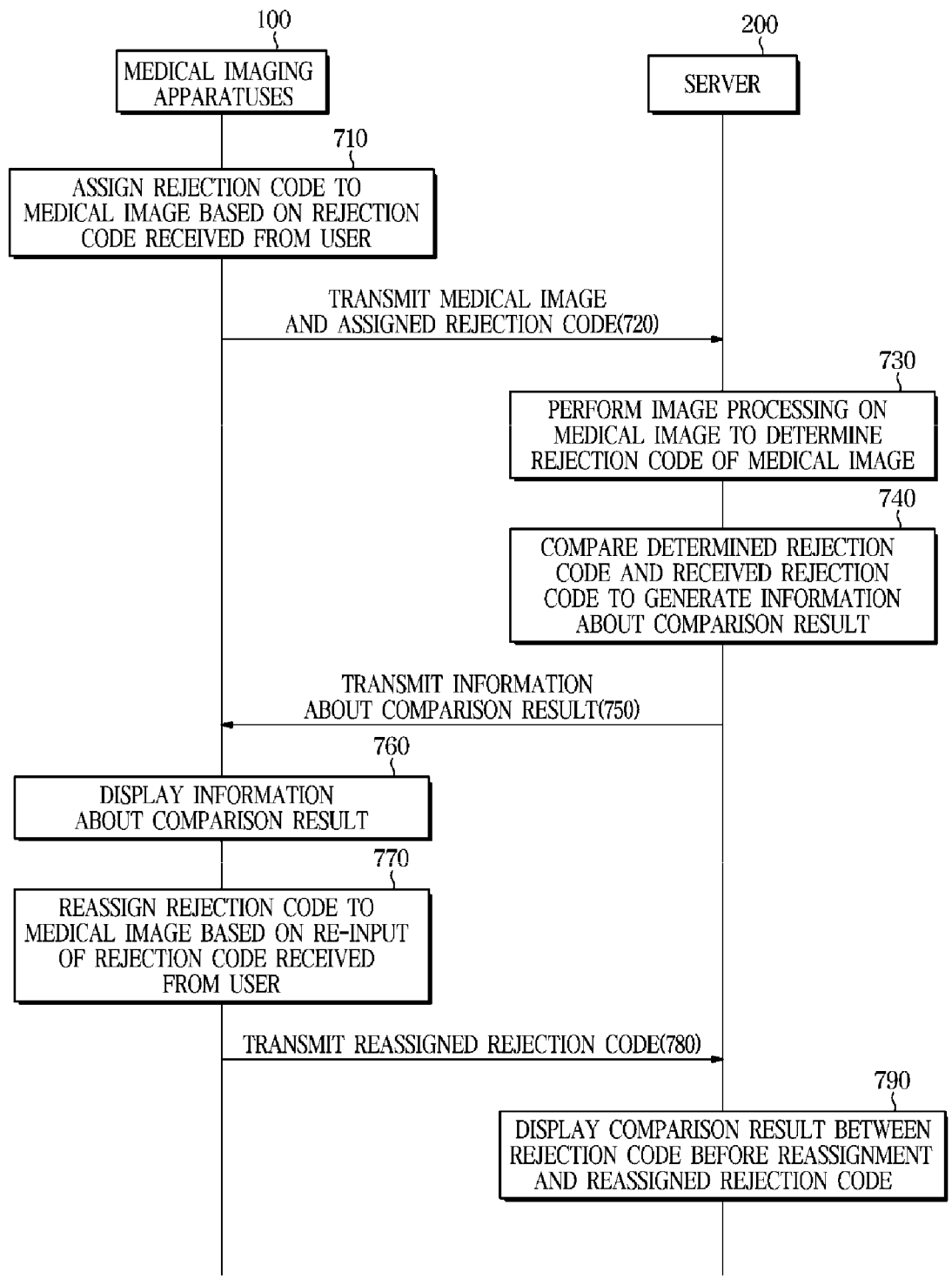
FIG. 8 is a view illustrating a signal flow for notifying a discrepancy of a rejection code according to embodiments of the disclosure.
Figure 9:
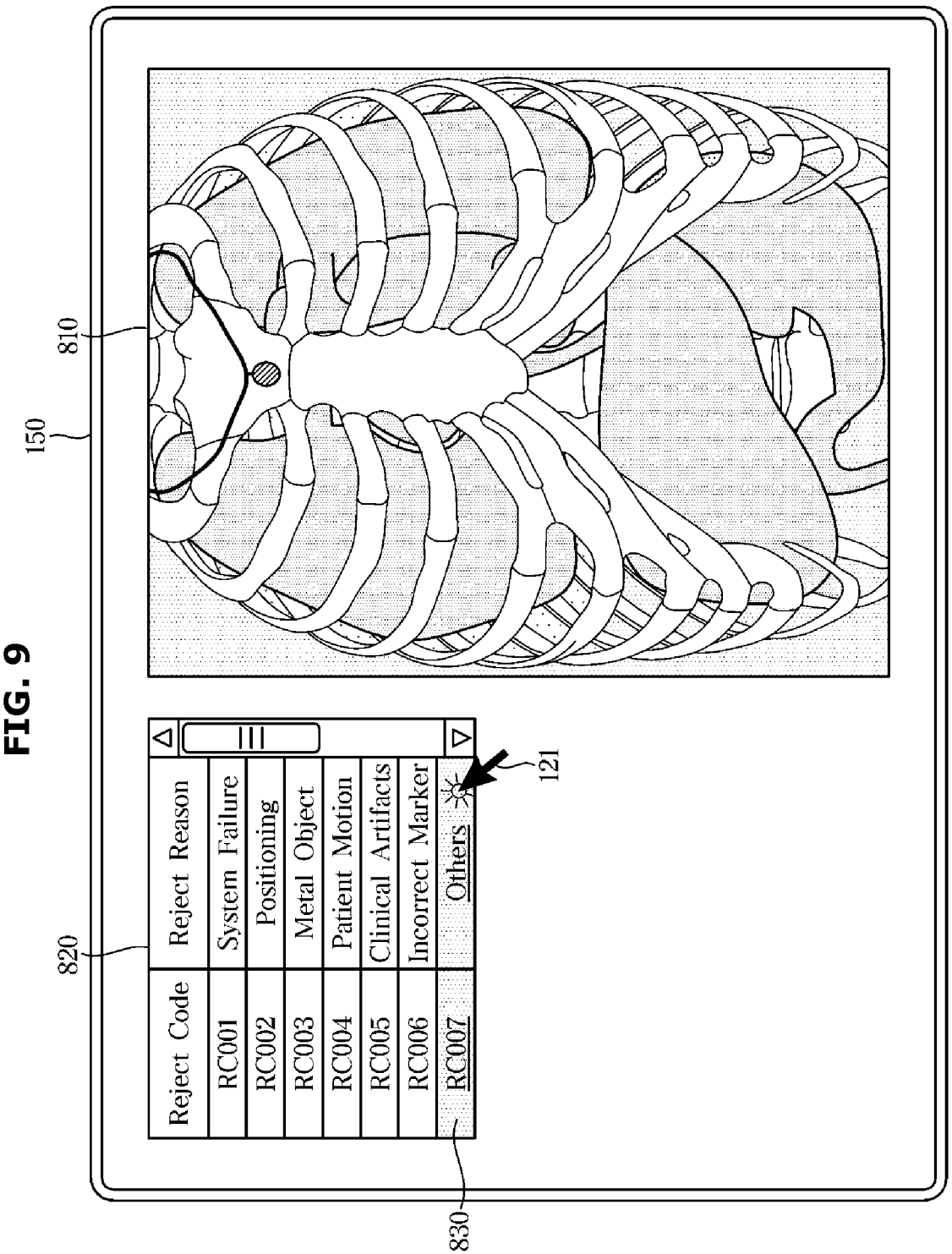
FIG. 9 is a view illustrating a case where a rejection code corresponding to a medical image is received in a medical imaging apparatus according to embodiments of the disclosure.
Figure 10:
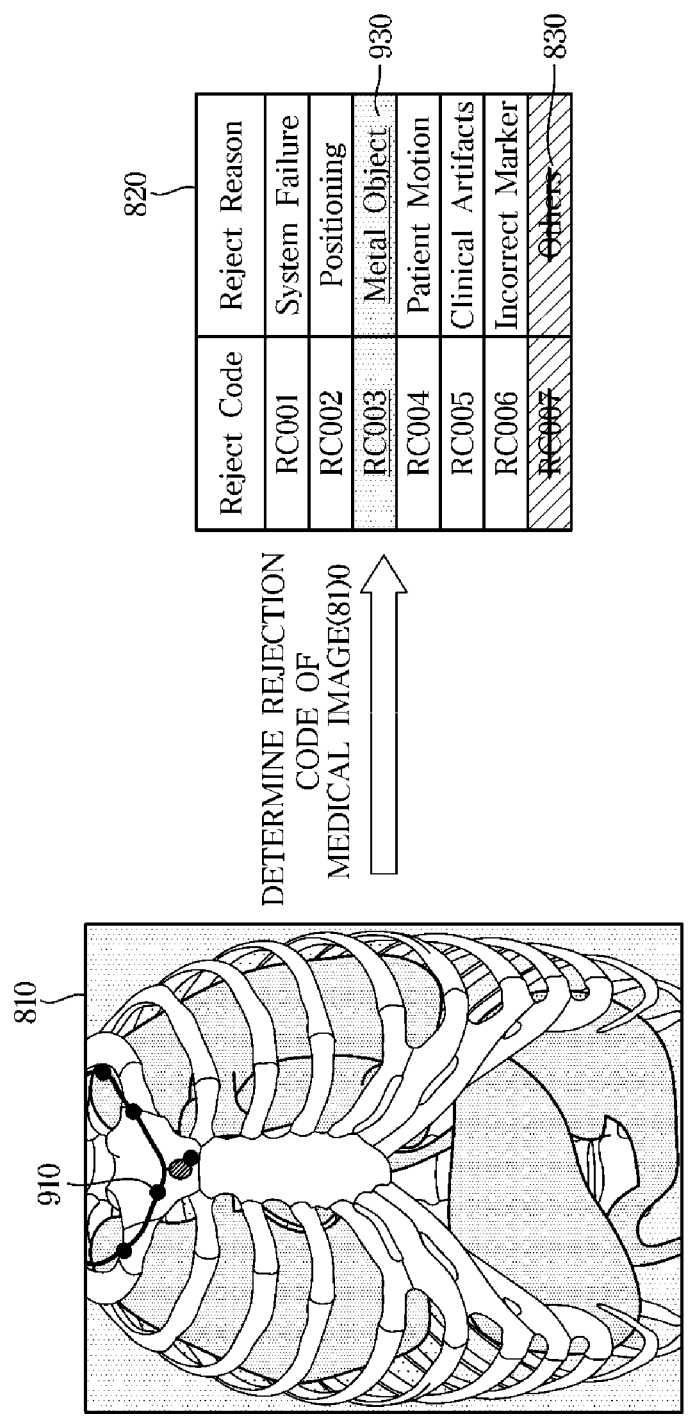
FIG. 10 is a view illustrating a case where a server determines a rejection code of a medical image according to embodiments of the disclosure.
Figure 11:
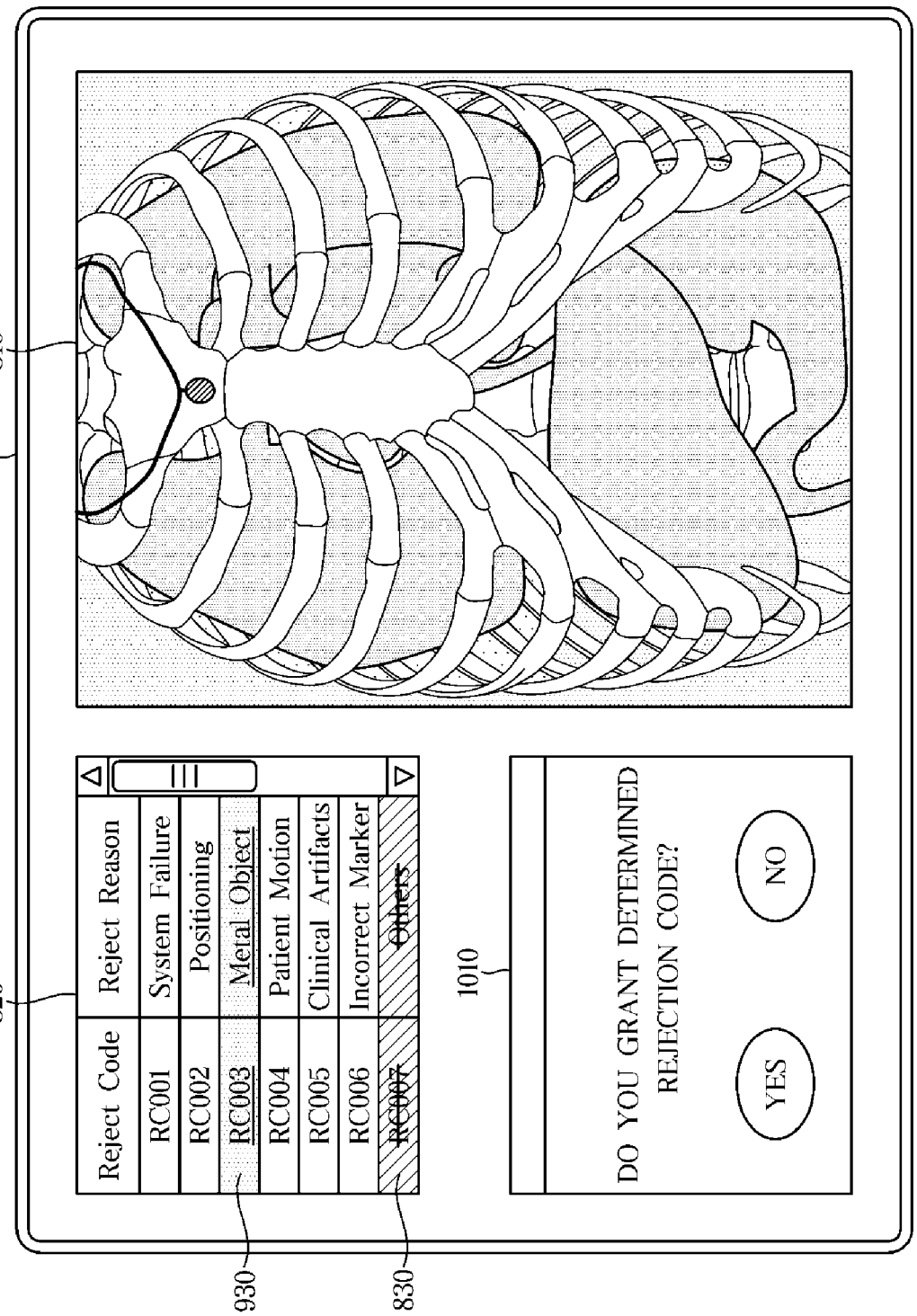
FIG. 11 is a view illustrating a case where a user approves a rejection code determined by a server according to embodiments of the disclosure.
Figure 12:
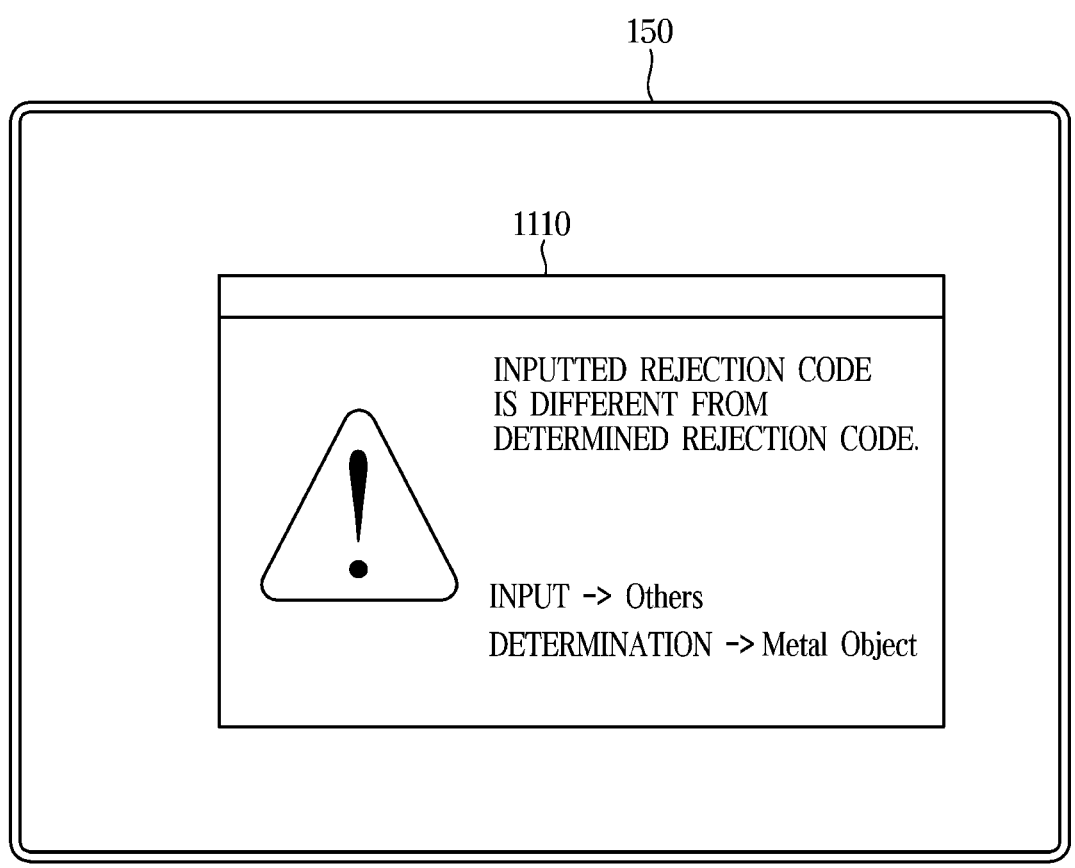
FIG. 12 is a view illustrating a case where information about a comparison result received from a server is displayed in a medical imaging apparatus according to embodiments of the disclosure.
Figure 13:
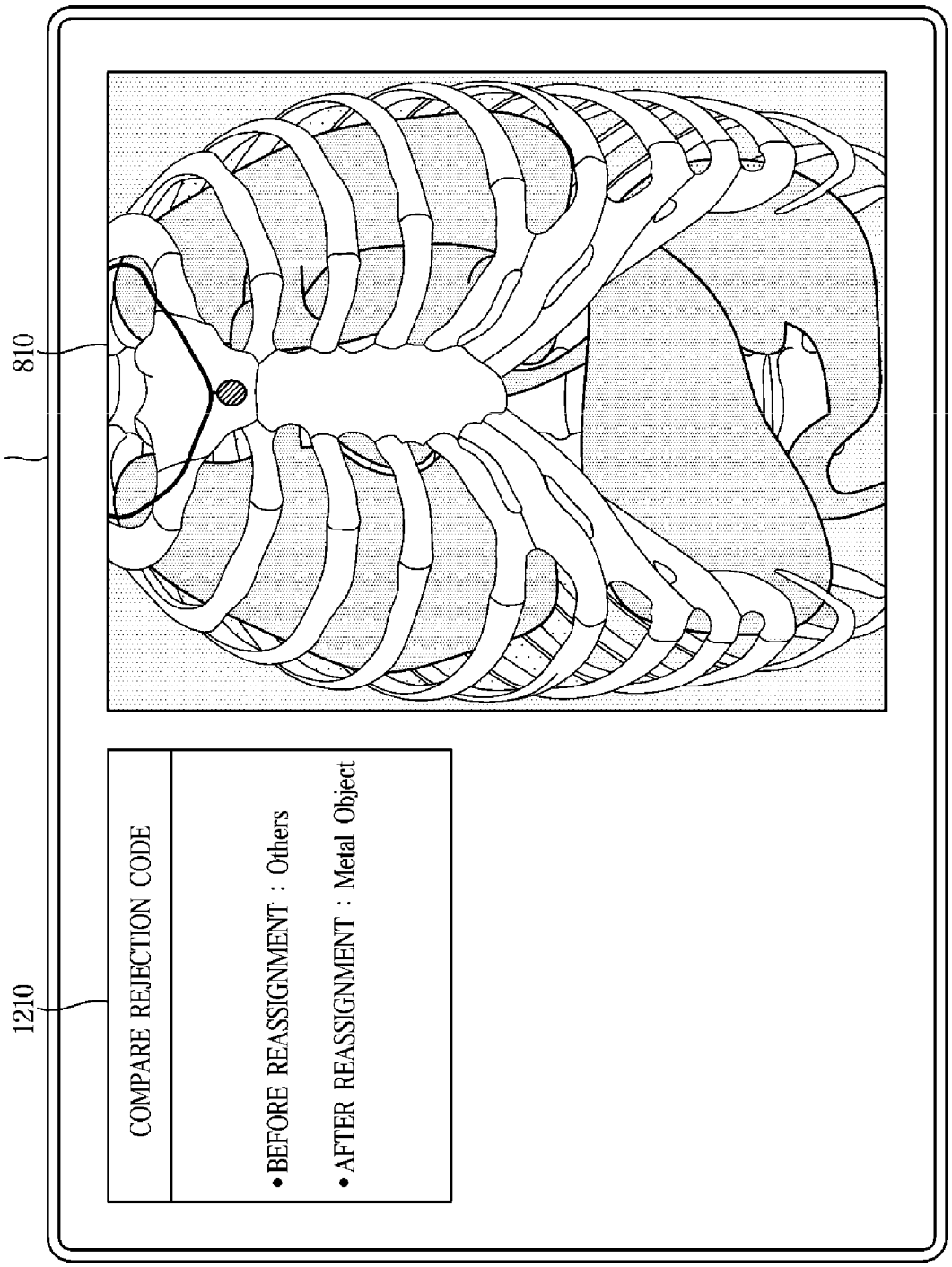
FIG. 13 is a view illustrating a case where a comparison result between a rejection code before reassignment and a reassigned rejection code is displayed in a server according to embodiments of the disclosure.

FIG. 8 is a view illustrating a signal flow for notifying a discrepancy of a rejection code according to embodiments of the disclosure, FIG. 9 is a view illustrating a case where a rejection code corresponding to a medical image is received in a medical imaging apparatus according to embodiments of the disclosure, FIG. 10 is a view illustrating a case where a server determines a rejection code of a medical image according to embodiments of the disclosure, FIG. 11 is a view illustrating a case where a user approves a rejection code determined by a server according to embodiments of the disclosure, FIG. 12 is a view illustrating a case where information about a comparison result received from a server is displayed in a medical imaging apparatus according to embodiments of the disclosure, and FIG. 13 is a view illustrating a case where a comparison result between a rejection code before reassignment and a reassigned rejection code is displayed in a server according to embodiments of the disclosure.

Referring to FIG. 8, the medical imaging apparatus 100 may assign the rejection code to the medical image based on the rejection code received from the user (710).

Particularly, the controller 140 of the medical imaging apparatus 100 may assign the rejection code to the medical image based on the rejection code for the medical image input from the user through the inputter 120.

For example, as illustrated in FIG. 9, the controller 140 of the medical imaging apparatus 100 may display a medical image 810 obtained through the capturer 110 and a predetermined rejection code for each rejection type 820 stored in the storage 160 on the display 150.

At this time, the user of the medical imaging apparatus 100 may review the displayed medical image 810 to determine whether the medical image 810 can be used for diagnosis. Further, when the medical image 810 is determined to be unusable for diagnosis, the user may reject the medical image 810 by selecting a rejection code 830 (i.e., the rejection type) corresponding to the reason why it cannot be used for diagnosis, on the displayed predetermined rejection code for each rejection type 820, through the inputter 120 (e.g., by moving the point 121 to the rejection code to be selected and clicking the rejection code).

For example, the user may select the rejection code 830 (e.g., RC007) for the rejection type (e.g., Others) other than the rejection type of the metal artifact, even though there is the rejection type of the metal artifact on the medical image 810 because the medical image 810 is captured under a condition in which the patient wears a metal necklace. That is, the user may perform erroneous determination or erroneous selections for the rejection type of the medical image 810. At this time, the controller 140 of the medical imaging apparatus 100 may assign the rejection code 830 inputted by the user to the medical image 810.

The medical imaging apparatus 100 may transmit the medical image 810 and the assigned rejection code 830 to the server 200 through the communication circuitry 130 (720).

At this time, the medical image 810 may correspond to the image that is determined not to be used for diagnosis, that is, the rejected image, and the rejection code 830 may correspond to the rejection reason, that is, the rejection type.

The server 200 may perform the image processing on the medical image 810 to determine the rejection code of the medical image 810 (730).

That is, the controller 230 of the server 200 may perform the image processing on the received medical image 810 and determine the rejection code of the medical image 810 separately from the received rejection code 830. In other words, the server 200 may analyze the medical image 810 by itself and determine the rejection code for the medical image 810.

At this time, the server 200 may determine the rejection code for the medical image 810 based on various methods. For example, the server 200 may determine the rejection code of the medical image 810 according to the image processing based on the image processing algorithm, and may determine the rejection code of the medical image 810 using the neural network provided in the storage 250. In addition, the server 200 may determine the rejection code for the medical image 810 by further considering the information about the system log or the information about the capturing condition.

Particularly, referring to FIG. 10, the controller 230 may extract feature points 910 of the medical image 810 and determine the rejection code 930 of the medical image 810 based on the extracted feature points 910 and information about the predetermined rejection code for each feature point.

At this time, the controller 230 may extract the feature points 910 in the medical image 810 by applying the image processing algorithm such as the object recognition algorithm. For example, the controller 230 may apply the edge detection to extract artifacts included in the medical image 810. In addition, the controller 230 may extract the artifacts included in the medical image 810 by extracting the types through morphological operations.

However, the image processing algorithm used to extract the feature points 910 is not limited to the above-described example, and may be used without limitation as long as it corresponds to the image processing algorithm capable of extracting the feature points 910 that can be included in the medical image 810.

At this time, the feature points 910 may correspond to at least one of the metal artifact caused by the metal located in the medical image 810, the motion artifact due to movement of the patient, such as respiration, and noise. However, the types of feature points 910 are not limited to the above-described example, and may be included without limitation as long as they are types of quality defects that can appear in the medical image 810.

For example, as illustrated in FIG. 10, the controller 230 may determine that the rejection type of the metal image 810 corresponds to the metal object based on the feature points 910 corresponding to the metal artifact extracted according to the image processing of the medical image 810, and the controller 230 may determine the rejection code (RC003) corresponding to the metal object as the rejection code 930 of the medical image 810 based on the determination.

Also, the controller 230 may determine the rejection code of the medical image through a neural network, without determining the rejection code based on the information about the predetermined rejection code for each feature point.

Particularly, the controller 230 may perform an operation on the received medical image through the neural network, and may determine the rejection code 930 of the medical image 810 based on the information about the operation performed through the neural network.

At this time, the information according to the operation through the neural network may include the information about rejection reason or rejection type of the medical image.

Since the above-described neural network may refer to a machine learning that forms the neural structure capable of performing deep learning, the weight and the bias corresponding to the configuration of the neural network continuously change, thereby improving the reliability of learning.

Particularly, the server 200 may continuously receive the medical image and the corresponding rejection code from the outside. The controller 230 may improve inference results of the neural network by continuously updating the weight, the bias, and activation functions included in the neural network based on the medical image and the corresponding rejection code received from the outside.

At this time, the neural network may be stored in storage 250 in the form of the computer program. Hereinafter the computation performed by the neural network in the coding form of the computer program will be described. However the disclosure is not limited to the computer program in which the neural network is stored.

Meanwhile, the neural network may include the Convolution Neural Network (CNN) for generating a feature map output by convoluting the medical image, and inputting the feature map to the neural network. However, the disclosure is not limited thereto, and may be performed by another deep learning algorithm including Recurrent Neural Networks (RNN).

In addition, the controller 230 may determine the rejection code 930 of the medical image 810 based on at least one of the result of the image processing (for example, the extracted result of the feature point according to the image processing algorithm, and the determination result of the rejection type according to the neural network), the information about a capturing condition assigned to the medical image, and the information about the system log of the medical imaging apparatus 100.

Particularly, in addition to the result of the image processing, the controller 230 may separately or further consider the information about the system log of the medical imaging apparatus 100 received together with the medical image 810 from the medical imaging apparatus 100 to determine that the rejection type of the medical image 810 is the system failure, and may determine the rejection code corresponding to the system failure as the rejection code 930 of the medical image 810.

In addition to the result of the image processing and the information about the system log, the controller 230 may separately or further consider the information about the capturing condition included in the header of the medical image 810 to determine that the rejection type of the medical image 810 is the capturing condition error, and may determine the rejection code corresponding to the capturing condition error as the rejection code 930 of the medical image 810.

Particularly, the controller 230 may identify a difference (for example, a difference in irradiation dose) from a standard protocol based on an imaging region based on information about a capturing protocol included in the information about the medical image 810. When a difference value equal to or greater than a threshold value occurs, the controller 230 may determine the rejection code corresponding to the capturing condition error as the rejection code 930 of the medical image 810.

The controller 230 may also determine the rejection code 930 of the medical image 810 based on the rejection code inputted by the user through the inputter 210. That is, the user of the server 200 may review the medical image 810 displayed on the display 240, determine the rejection type of the medical image 810, and input the rejection code by selecting the corresponding rejection code.

The server 200 may compare the determined rejection code 930 and the rejection code 830 received from the medical imaging apparatus 100 to generate information about the comparison result (740).

At this time, the received rejection code 830 and the determined rejection code 930 may differ depending on the determination error or a selection error of the user of the medical imaging apparatus 100, as illustrated in FIG. 10.

The server 200 may transmit the information about the comparison result to the medical imaging apparatus 100 when the determined rejection code 930 and the received rejection code 830 are different (750).

That is, when the rejection code 930 determined by the controller 230 is different from the rejection code 830 received from the medical imaging apparatus 100, the controller 230 may provide feedback that the rejection code 930 determined by the medical imaging apparatus 100 is different from the received rejection code 830 so that the user of the medical imaging apparatus 100 can determine his/her judgment once more.

In addition, the server 200 may further include a user's approval processing for the rejection code 930 determined by the controller 230.

Particularly, through the inputter 210, the controller 230 may receive the user's input granting the determined rejection code 930.

For example, as illustrated in FIG. 11, the controller 230 may control the display 240 to display a message 1010 identifying whether the determined rejection code 930 has been granted. At this time, through the inputter 210, the user may input the input (e.g., click on "YES" on the displayed message 1010) for granting the determined rejection code 930 in response to the displayed message 1010.

That is, the user of the server 200 may review the medical image 810 displayed on the display 240 and the determined rejection code 930 to determine whether the determined rejection code 930 corresponds to the rejection reason or rejection type of the medical image 810. When it is determined that the determined rejection code 930 corresponds to the rejection type of the medical image 810, the user may input the input for granting the determined rejection code 930 through the inputter 210.

In this case, the controller 230 may proceed to the feedback to the medical imaging apparatus 100 by controlling the communication circuitry 220 to transmit the information about the comparison result of the determined rejection code 930 and the received rejection code 830 to the medical imaging apparatus 100.

Through the inputter 210, the controller 230 may also receive the input from the user who is non-granting the determined rejection code 930.

That is, when the user of the server 200 determines that the determined rejection code 930 does not correspond to the rejection type of the medical image 810, the user may input the input for non-granting the determined rejection code 930 through the inputter 210. For example, through the inputter 210, the user may input the input (e.g., click on "NO" on the displayed message 1010) for non-granting the determined rejection code 930 in response to the displayed message 1010.

In this case, the controller 230 may perform the image processing on the medical image 810 again to determine the rejection code 930 of the medical image 810 again.

When receiving the comparison result, which represents that the assigned rejection code 830 and the rejection code 930 determined by the server 200 are different from each other, from the server 200 through the communication circuitry 130, the medical imaging apparatus 100 may control the display 150 to display the comparison result (760).

For example, the controller 140 of the medical imaging apparatus 100 may control the display 150 to display a message 1110 for the comparison result representing that the inputted rejection code 830 and the rejection code 930 determined by the server 200 are different from each other, as illustrated in FIG. 12.

At this time, the displayed message 1110 may include the information about the rejection type corresponding to the inputted rejection code 830 and the rejection code 930 determined by the server 200, respectively.

For this, the user may identify that the rejection code 830 inputted by himself or herself is different from the rejection code 930 determined by the server 200, and may re-input the correct rejection code through the inputter 120.

In this case, the medical imaging apparatus 100 may reassign the rejection code to the medical image 810 based on re-input of the rejection code received from the user (770).

The medical imaging apparatus 100 may also transmit the reassigned rejection code to the server 200 when the rejection code for the medical image 810 is reassigned from the user through the inputter 120 (780).

When the server 200 receives the reassigned rejection code from the medical imaging apparatus 100, the server 200 may display the comparison result between the rejection code before reassignment and the reassigned rejection code (790).

Particularly, the controller 230 may receive the rejection code reassigned from the medical imaging apparatus 100 to the medical image through the communication circuitry 220 after transmission of the comparison result between the determined rejection code 930 and the received rejection code 830 to the medical imaging apparatus 100.

In this case, the controller 230 may compare the rejection code before reassignment and the reassigned rejection code to generate the comparison result, and as illustrated in FIG. 13, control the display 240 to display a message 1210 representing the comparison result between the rejection code before reassignment and the reassigned rejection code. At this time, the rejection code before reassignment may correspond to rejection code 830 received prior to feedback to medical imaging apparatus 100, and the displayed message 1210 may include the information about the rejection type corresponding to each of the rejection code before reassignment and reassigned.

In this way, the user of the server 200 may determine whether or not the rejection code for the medical image 810 has been correctly assigned in response to the feedback of the server 200 by the user of the medical imaging apparatus 100.

In addition, the server 200 may update the statistical information about each medical imaging apparatus 100 based on the medical image and the corresponding rejection code.

Particularly, when the determined rejection code and the received rejection code are the same, the controller 230 may control the storage 250 to store the medical image and the received rejection code in the statistical information corresponding to the medical imaging apparatus 100.

When receiving the reassigned rejection code for the medical image, the controller 230 may also control the storage 250 to store the medical image and the reassigned rejection code in the statistical information corresponding to the medical imaging apparatus 100.

In this case, the statistical information may include information about the ratio of rejected medical images among the medical images captured by the medical imaging apparatus 100 and statistical information about the rejection reasons or rejection type of the rejected medical images.

Hereinafter a method of controlling the medical imaging apparatus 100 and the server 200 according to embodiments will be described. The medical imaging apparatus 100 and the server 200 may be applied to the medical imaging apparatus 100 and the server 200 above-described. The contents described with reference to FIGS. 1 to 13 may be equally applicable to the method of controlling the medical imaging apparatus 100 and the server 200 according to the embodiments without any particular reference.

Figure 14:
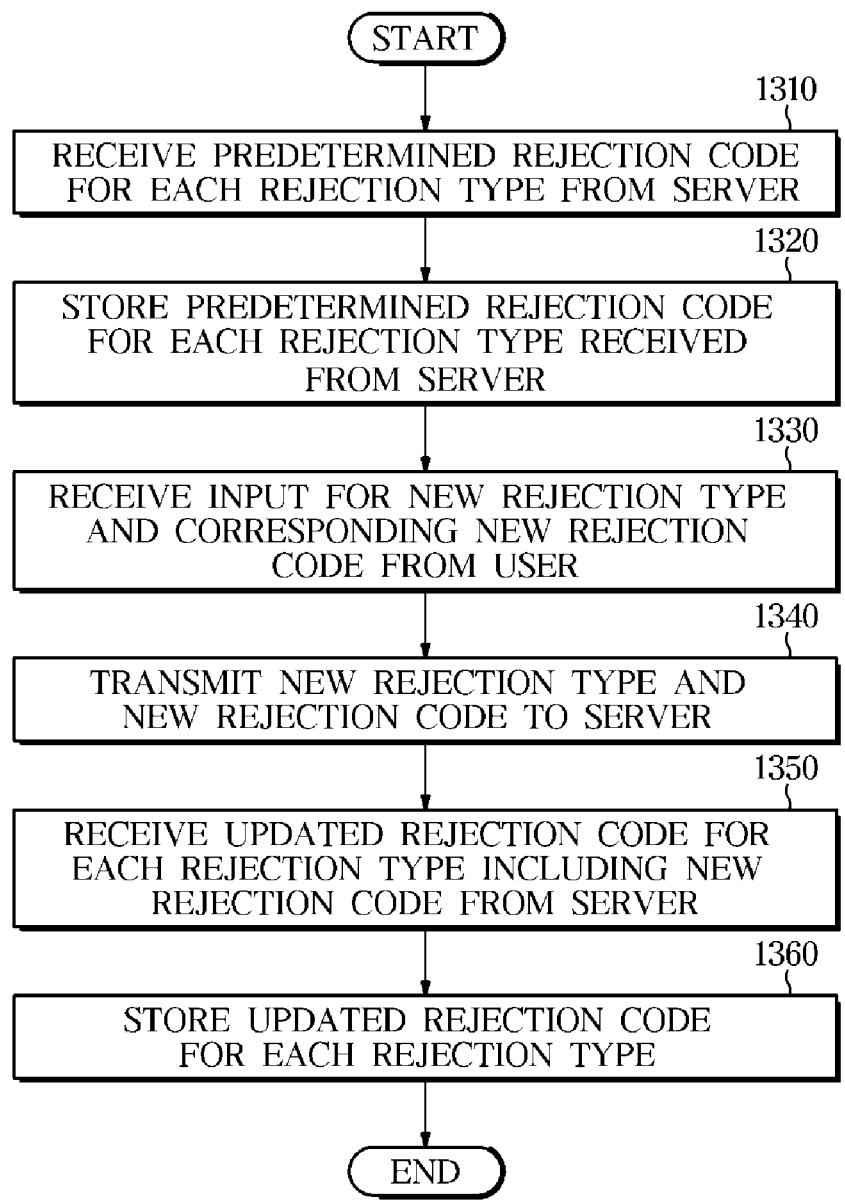
FIG. 14 is a flowchart illustrating a case where a rejection code for each rejection type is stored in a method of controlling a medical imaging apparatus according to embodiments of the disclosure.

FIG. 14 is a flowchart illustrating a case where a rejection code for each rejection type is stored in a method of controlling a medical imaging apparatus 100 according to embodiments of the disclosure.

Referring to FIG. 14, the medical imaging apparatus 100 may receive the predetermined rejection code for each rejection type from the server 200 (1310).

In addition, the medical imaging apparatus 100 may store the predetermined rejection code for each rejection type received from the server 200 (1320).

Particularly, the controller 140 may also control the storage 160 to store the rejection code for each rejection type received from the server 200 through the communication circuitry 130.

That is, the medical imaging apparatus 100 uses the rejection code for each rejection type received from the server 200 through the communication circuitry 130, thus the plurality of medical imaging apparatuses 100 connected to the server 200 may use the rejection code for the same rejection type.

Accordingly, the server 200 may more efficiently manage the medical images of the medical imaging apparatus 100 and the corresponding rejection codes, and may ensure the consistency of the statistical information.

The medical imaging apparatus 100 may also receive the input for the new rejection type and the corresponding new rejection code from the user (1330), and may transmit the new rejection type and the new rejection code to the server 200 (1340).

That is, when the new rejection type, which is other than the rejection type included in the stored rejection code for each rejection type and the new rejection code corresponding to the new rejection type are inputted from the user through the inputter 120 the controller 140 may control the communication circuitry 130 to transmit the new rejection type and the new rejection code to the server 200.

In other words, when there is no the rejection type corresponding to the medical image obtained on the rejection code for each rejection type provided from the server 200, the user may manually input the rejection type and the rejection code corresponding to the rejection type, thereby generating the new rejection type and the new rejection code.

The communication circuitry 130 of the imaging apparatus 100 may transmit the generated new rejection type and new rejection code to the server 200 so that the new rejection type and the new rejection code generated by the medical imaging apparatus 100 are also shared with other medical imaging apparatuses 100 so that the plurality of medical imaging apparatuses 100 connected to the server 200 use a consistent rejection code for each type rejection type.

At this time, the server 200 may update the predetermined rejection code for each rejection type to include the received new rejection type and the new rejection code, and may transmit the updated rejection code for each rejection type to the plurality of medical imaging apparatuses 100 connected through the network 300.

That is, the medical imaging apparatus 100 may receive the updated rejection code for each rejection type including the new rejection code from the server 200 (1350). At this time, the new rejection code included in the updated rejection code for each rejection type may be generated by another medical imaging apparatus other than the medical imaging apparatus 100 that received the updated rejection code for each rejection type.

The medical imaging apparatus 100 may store the updated rejection code for each rejection type (1360).

Particularly, when receiving the updated rejection code for each rejection type different from the stored rejection code for each rejection type from the server 200, the controller 140 of each medical imaging apparatus 100 connected to the server 200 through the network 300 may control the storage 160 to store the updated rejection code for each rejection type.

Figure 15:
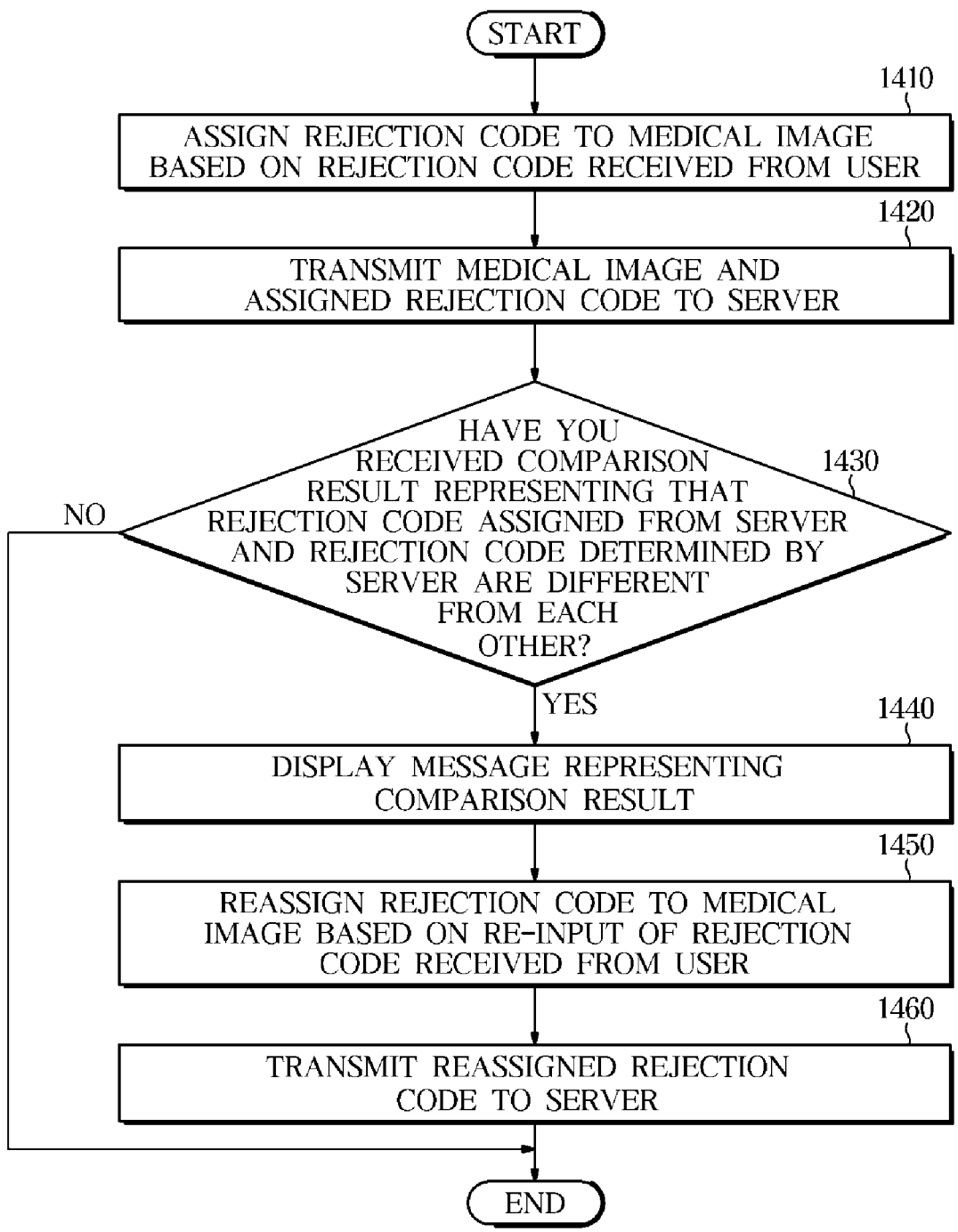
FIG. 15 is a flowchart illustrating a case where a rejection code is assigned to a medical image in a method of controlling a medical imaging apparatus according to embodiments of the disclosure.

FIG. 15 is a flowchart illustrating a case where a rejection code is assigned to a medical image in a method of controlling a medical imaging apparatus 100 according to embodiments of the disclosure.

Referring to FIG. 15, the medical imaging apparatus 100 may assign the rejection code to the medical image based on the rejection code received from the user (1410).

Particularly, the controller 140 of the medical imaging apparatus 100 may assign the rejection code to the medical image based on the rejection code for the medical image input from the user through the inputter 120.

The medical imaging apparatus 100 may transmit the medical image 810 and the assigned rejection code 830 to the server 200 (1420).

At this time, the medical image 810 may correspond to the image that is determined not to be used for diagnosis, that is, the rejected image, and the rejection code 830 may correspond to the rejection reason, that is, the rejection type.

When receiving the comparison result representing that the assigned rejection code 830 and the rejection code 930 determined by the server 200 are different from each other, from the server 200 through the communication circuitry 130 (YES in 1430), the medical imaging apparatus 100 may display the message 1110 representing the comparison result (1440).

At this time, the displayed message 1110 may include the information about the rejection type corresponding to the inputted rejection code 830 and the rejection code 930 determined by the server 200, respectively.

For this, the user may identify that the rejection code 830 inputted by the user is different from the rejection code 930 determined by the server 200, and may re-input the correct rejection code through the inputter 120.

In this case, the medical imaging apparatus 100 may reassign the rejection code to the medical image 810 based on re-input of the rejection code received from the user (1450).

The medical imaging apparatus 100 may also transmit the reassigned rejection code to the server 200 when the rejection code for the medical image 810 is reassigned from the user through the inputter 120 (1460).

Figure 16:
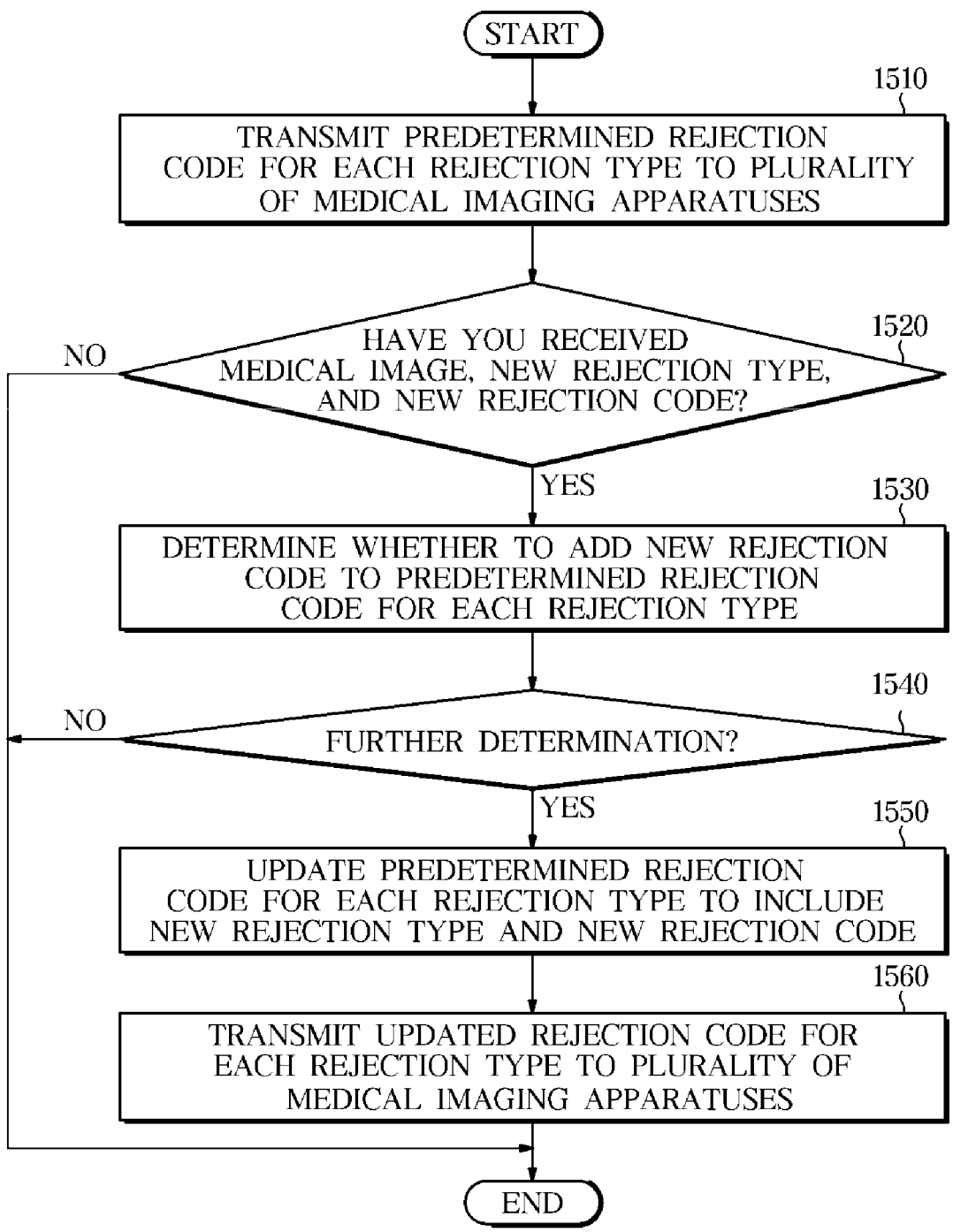
FIG. 16 is a flowchart illustrating a case where a rejection code for each rejection type is managed in a method of controlling a server according to embodiments of the disclosure.

FIG. 16 is a flowchart illustrating a case where a rejection code for each rejection type is managed in a method of controlling a server 200 according to embodiments of the disclosure.

Referring to FIG. 16, the server 200 may transmit the predetermined rejection code for each rejection type to the plurality of medical imaging apparatuses 100 (1510).

The predetermined rejection code for each rejection type may be preset in the design stage of the server 200 and stored in the storage 250, and may be also be received from the external server through the communication circuitry 220 and stored in the storage 250.

Each of the medical imaging apparatuses 100 may use the same rejection code for each rejection type by using the rejection code for each rejection type received from the server 200 through the communication circuitry 130.

Accordingly, the server 200 may more efficiently manage the medical image of each of the medical imaging apparatuses 100 and the corresponding rejection code and ensure the consistency of the statistical information.

When receiving the medical image, the new rejection type, and the new rejection code (YES in 1520), the server 200 may determine whether to add the new rejection code to the predetermined rejection code for each rejection type (1530).

The communication circuitry 130 of the imaging apparatus 100 may transmit the generated new rejection type and new rejection code to the server 200 so that the new rejection type and the new rejection code generated by the medical imaging apparatus 100 are also shared with other medical imaging apparatuses 100 so that the plurality of medical imaging apparatuses 100 connected to the server 200 use a consistent rejection code for each type rejection type.

At this time, the controller 230 of the server 200 may perform the image processing on the medical image 610 transmitted together with the new rejection code to determine the rejection type of the medical image 610, and may determine whether to add the new rejection code to the predetermined rejection code for each rejection type by determining whether the determined rejection type corresponds to the received new rejection type. At this time, the controller 230 may further consider the frequency of the new rejection type, that is, the frequency of reception from the medical imaging apparatus 100 for the new rejection type, to determine whether to add the new rejection code to the rejection code for each rejection type.

That is, the server 200 may update the predetermined rejection code for each rejection type by including the new rejection code in the predetermined rejection code for each rejection type when the determined rejection type corresponds to the received new rejection type.

In other words, when the server 200 determines to add the new rejection code to the predetermined rejection code for each rejection type (YES in 1540), the server 200 may update the predetermined rejection code for each rejection type to include the new rejection type and the new rejection code (1550).

However, when receiving the new rejection type and the new rejection code, the server 200 may update the predetermined rejection code for each rejection type based on the received new rejection type and the new rejection code without the determination of whether or not to add.

In addition, the server 200 may transmit the updated rejection code for each rejection type to the plurality of medical imaging apparatuses 100 (1560).

Figure 17:
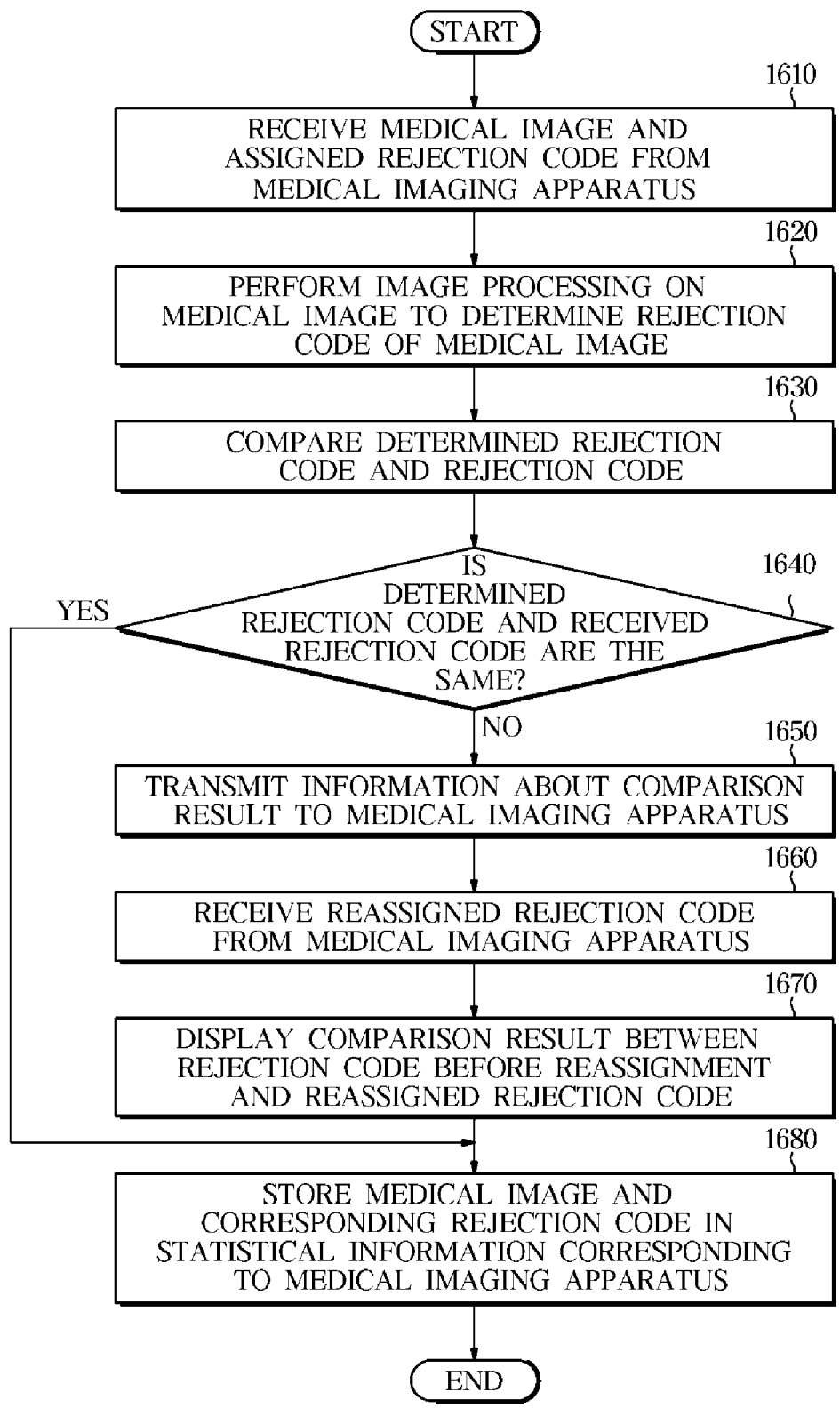
FIG. 17 is a flowchart illustrating a case where a discrepancy of a rejection code assigned to a medical image is notified in a method of controlling a server according to embodiments of the disclosure.

FIG. 17 is a flowchart illustrating a case where a discrepancy of a rejection code assigned to a medical image is notified in a method of controlling a server 200 according to embodiments of the disclosure.

Referring to FIG. 17, the server 200 may receive the medical image 810 and the assigned rejection code 830 from the medical imaging apparatus 100 (1610).

At this time, the medical image 810 may correspond to the image that is determined not to be used for diagnosis, that is, the rejected image, and the rejection code 830 may correspond to the rejection reason, that is, the rejection type.

The server 200 may perform the image processing on the medical image 810 to determine the rejection code of the medical image 810 (1620).

That is, the controller 230 of the server 200 may perform the image processing on the received medical image 810 and determine the rejection code of the medical image 810 separately from the received rejection code 830. In other words, the server 200 may analyze the medical image 810 by itself and determine the rejection code for the medical image 810.

At this time, the server 200 may determine the rejection code for the medical image 810 based on various methods. For example, the server 200 may determine the rejection code of the medical image 810 according to the image processing based on the image processing algorithm, and may determine the rejection code of the medical image 810 using the neural network provided in the storage 250. In addition, the server 200 may determine the rejection code for the medical image 810 by further considering the information about the system log or the information about the capturing condition. In addition, the server 200 may determine the rejection code inputted through the inputter 210 from the user of the server 200 as the rejection code of the medical image 810. The description of the methods of determining the rejection code for the medical image 810 is the same as that described with reference to FIG. 8, so that a detailed description of each method will be omitted.

The server 200 may compare the determined rejection code 930 and the rejection code 830 received from the medical imaging apparatus 100 (1630).

At this time, the received rejection code 830 and the determined rejection code 930 may differ depending on the determination error or a selection error of the user of the medical imaging apparatus 100.

When the determined rejection code 930 and the received rejection code 830 are not the same (NO in 1640), the server 200 may control the communication circuitry 220 to transmit the information about the comparison result to the medical imaging apparatus 100 (1650).

That is, when the rejection code 930 determined by the controller 230 is different from the rejection code 830 received from the medical imaging apparatus 100, the controller 230 may provide feedback that the rejection code 930 determined by the medical imaging apparatus 100 is different from the received rejection code 830 so that the user of the medical imaging apparatus 100 can determine his/her judgment once more.

For this, the user may identify that the rejection code 830 inputted by himself of herself is different from the rejection code 930 determined by the server 200, and may re-input the correct rejection code through the inputter 120.

In this case, the medical imaging apparatus 100 may reassign the rejection code to the medical image 810 based on re-input of the rejection code received from the user.

The medical imaging apparatus 100 may also transmit the reassigned rejection code to the server 200 when the rejection code for the medical image 810 is reassigned from the user through the inputter 120.

The server 200 may receive the reassigned rejection code from the medical imaging apparatus 100 (1660), and may display the comparison result between the rejection code before reassignment and the reassigned rejection code (1670).

Particularly, the controller 230 may receive the rejection code reassigned from the medical imaging apparatus 100 to the medical image through the communication circuitry 220 after transmission of the comparison result between the determined rejection code 930 and the received rejection code 830 to the medical imaging apparatus 100.

In this case, the controller 230 may compare the rejection code before reassignment and the reassigned rejection code to generate the comparison result, and control the display 240 to display a message 1210 representing the comparison result between the rejection code before reassignment and the reassigned rejection code.

At this time, the rejection code before reassignment may correspond to rejection code 830 received prior to feedback to medical imaging apparatus 100, and displayed message 1210 may include the information about the rejection type corresponding to each of the rejection code before reassignment and reassigned.

In this way, the user of the server 200 may determine whether or not the rejection code for the medical image 810 has been correctly assigned in response to the feedback of the server 200 by the user of the medical imaging apparatus 100.

In addition, the server 200 may store the medical image 810 and the corresponding rejection code in the statistical information corresponding to the medical imaging apparatus 100 (1680).

That is, the server 200 may update the statistical information about each medical imaging apparatus 100 based on the medical image and the corresponding rejection code.

Particularly, when the determined rejection code and the received rejection code are the same (YES in 1640), the controller 230 may control the storage 250 to store the medical image and the received rejection code in the statistical information corresponding to the medical imaging apparatus 100.

When receiving the reassigned rejection code for the medical image, the controller 230 may also control the storage 250 to store the medical image and the reassigned rejection code in the statistical information corresponding to the medical imaging apparatus 100.

In this case, the statistical information may include information about the ratio of rejected medical images among the medical images captured by the medical imaging apparatus 100 and statistical information about the rejection reasons or rejection type of the rejected medical images.

As is apparent from the above description, it is possible to efficiently and accurately manage the statistical information about the rejection codes for the medical image for each medical imaging apparatus by collectively managing the rejection codes for each rejection type of the medical image and determining the accuracy of the rejection codes for the medical image transmitted from the medical imaging apparatus and providing the feedback.

Meanwhile, the disclosed embodiments may be implemented in the form of a recording medium storing instructions that are executable by a computer. The instructions may be stored in the form of a program code, and when executed by a processor, the instructions may generate a program module to perform operations of the disclosed embodiments. The recording medium may be implemented as a computer-readable recording medium.

The computer-readable recording medium may include all kinds of recording media storing commands that can be interpreted by a computer. For example, the computer-readable recording medium may be ROM, RAM, a magnetic tape, a magnetic disc, flash memory, an optical data storage device, etc.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A server comprising:
a communication circuitry configured to communicate with a medical imaging apparatus; and
a controller configured to:
control the communication circuitry to receive a medical image and a first rejection code from the medical imaging apparatus, the first rejection code being obtained through the medical imaging apparatus, corresponding to an indicator of unuseability of the medical image for diagnosis and being assigned to the medical image by the medical imaging apparatus;
perform an image processing on the medical image to determine a second rejection code corresponding to an indicator of unuseability of the medical image for diagnosis of the medical image;
determine whether to transmit, to the medical imaging apparatus, information generated in association with a result of a comparison between the first rejection code received from the medical imaging apparatus and the second rejection code determined from the image processing; and
control the communication circuitry to transmit the information associated with the result of the comparison to the medical imaging apparatus when the first rejection code and the second rejection code are different.

2. The server according to claim 1, wherein the controller is configured to extract feature points of the medical image, and to determine the second rejection code of the medical image based on the extracted feature points and information associated with a predetermined rejection code for each feature points.

3. The server according to claim 1, wherein the controller is configured to perform an arithmetic operation on the medical image through a neural network, and to determine the second rejection code of the medical image based on information related to the arithmetic operation performed through the neural network.

4. The server according to claim 1, wherein the controller is configured to determine the second rejection code of the medical image based on at least one of a result of the image processing, information associated with a capturing condition assigned to the medical image, and information associated with a system log of the medical imaging apparatus.

5. The server according to claim 1, further comprising:
a display,
wherein the controller is configured to control the display to display at least one of the medical image, the second rejection code, and the information associated with the result of the comparison.

6. The server according to claim 5, further comprising:
an inputter configured to receive an input from a user,
wherein the controller is configured to:
when the input from the user granting the second rejection code is received through the inputter, transmit the information associated with the result to the medical imaging apparatus; and
when the input from the user non-granting the second rejection code through the inputter is received, perform the image processing on the medical image again to re-determine the second rejection code of the medical image.

7. The server according to claim 5, wherein, when a first rejection code reassigned from the medical imaging apparatus to the medical image is received through the communication circuitry after transmitting the result of the comparison, the controller is configured to control the display to display the result of the comparison before reassignment and the reassigned first rejection code.

8. The server according to claim 5, further comprising:
a storage,
wherein the controller is configured to:
when the second rejection code and the first rejection code are the same, control the storage to store the medical image and the first rejection code in association with statistical information corresponding to the medical imaging apparatus;
when a first rejection code reassigned to the medical image is received, control the storage to store the medical image and the reassigned first rejection code in association with the statistical information corresponding to the medical imaging apparatus; and
control the communication circuitry to transmit a predetermined rejection code for each rejection type to the medical imaging apparatus which is among a plurality of medical imaging apparatuses.

9. The server according to claim 8, wherein the controller is configured to:

when a new rejection type other than the rejection type included in the predetermined rejection code for each rejection type and a new rejection code corresponding to the new rejection type is received from at least one medical imaging apparatus among the plurality of medical imaging apparatuses, update the predetermined rejection code for each rejection type to include the new rejection code corresponding to the new rejection type to the predetermined rejection code for each rejection type; and control the communication circuitry to transmit the updated rejection code for each rejection type to the plurality of medical imaging apparatuses.

10. A medical imaging apparatus comprising:
a display;
a communication circuitry configured to communicate with a server;
an inputter configured to receive an input from a user;
a capturer configured to capture a medical image of an object; and
a controller configured to:
when a first rejection code indicating unuseability of the medical image for diagnosis of the medical image is assigned from the user through the inputter, control the communication circuitry to transmit the medical image and the first rejection code to the server; and
when a result of a comparison of the first rejection code transmitted to the server and a second rejection code indicating unuseability of the medical image for diagnosis of the medical image according to an image processing differ from each other, control the display to display the result of the comparison.

11. The medical imaging apparatus according to claim 10, wherein, when the first rejection code for the medical image is reassigned from the user through the inputter, the controller is configured to control the communication circuitry to transmit the reassigned first rejection code to the server.

12. The medical imaging apparatus according to claim 10, further comprising:
a storage,
wherein the controller is configured to control the storage to store the first rejection code for each rejection type received from the server through the communication circuitry.

13. The medical imaging apparatus according to claim 12, wherein, when the new rejection type other than the rejection type included in the first rejection code for each rejection type and the new rejection code corresponding to the new rejection type are input from the user through the inputter, the controller is configured to control the communication circuitry to transmit the new rejection type and the new rejection code to the server.

14. The medical imaging apparatus according to claim 12, wherein, when an updated rejection code for each rejection type different from the stored rejection code for each rejection type is received from the server, the controller is configured to control the storage to store the updated rejection code for each rejection type.

15. A method of controlling a medical imaging apparatus including a display, a communication circuitry configured to communicate with a server, an inputter configured to receive an input from a user, and a capturer configured to capture a medical image of an object, the method comprising:
when a first rejection code for the medical image is assigned from the user through the inputter, controlling, by a controller, the communication circuitry to transmit the medical image and the first rejection code to the server; and
when receiving a result of a comparison of the first rejection code from the server and a second rejection code determined by the server are different from each other, controlling, by the controller, the display to display the result of the comparison.

16. The method according to claim 15, further comprising:
when the first rejection code for the medical image is reassigned from the user through the inputter, controlling, by the controller, the communication circuitry to transmit the reassigned first rejection code to the server.

17. The method according to claim 15, wherein the medical imaging apparatus further comprises a storage, and the method further comprises:
controlling, by the controller, the storage to store the first rejection code for each rejection type received from the server through the communication circuitry.

18. The method according to claim 17, further comprising:
when the new rejection type other than the rejection type included in the first rejection code for each rejection type and the new rejection code corresponding to the new rejection type are input from the user through the inputter, controlling, by the controller, the communication circuitry to transmit the new rejection type and the new rejection code to the server.

19. The method according to claim 17, further comprising:
when an updated rejection code for each rejection type different from the stored rejection code for each rejection type is received from the server, controlling, by the controller, the storage to store the updated rejection code for each rejection type.

* * * * *